(12) United States Patent  (10) Patent No.: US 7,764,996 B2
Zhang et al.  (45) Date of Patent: Jul. 27, 2010

(54) MONITORING OF CHRONOBIOLOGICAL RHYTHMS FOR DISEASE AND DRUG MANAGEMENT USING ONE OR MORE IMPLANTABLE DEVICE

(75) Inventors: Yi Zhang, Blaine, MN (US); John D. Hatlestad, Maplewood, MN (US); Gerrard M. Carlson, Champlin, MN (US); Yousufali Dalal, St. Louis Park, MN (US); Marina V. Brockway, Shoreview, MN (US); Kent Lee, Shoreview, MN (US); Richard O. Kuenzler, Shaker Heights, OH (US); Carlos Haro, St. Paul, MN (US); Krzysztof Z. Siejko, Maple Grove, MN (US); Abhilash Patangay, Little Canada, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 860 days.

(21) Appl. No.: 11/554,986

(22) Filed: Oct. 31, 2006

(65) Prior Publication Data

US 2008/0114219 A1    May 15, 2008

(51) Int. Cl.
 *A61B 5/00* (2006.01)
(52) U.S. Cl. .................. 607/3; 600/301; 607/4
(58) Field of Classification Search ........... 607/4–25; 128/419; 600/528, 514; 604/67, 500
 See application file for complete search history.

(56) References Cited

U.S. PATENT DOCUMENTS

| 4,719,920 A | 1/1988 | Alt et al. |
| 4,922,930 A | 5/1990 | Adkins et al. |
| 5,143,065 A | 9/1992 | Adkins et al. |
| 5,607,459 A | 3/1997 | Paul et al. |
| 5,697,884 A | 12/1997 | Francischelli et al. |

(Continued)

FOREIGN PATENT DOCUMENTS

WO   WO-2006/050717 A1   5/2006

OTHER PUBLICATIONS

Aronow, W. S., et al., "Circadian variation of death from congestive heart failure after prior myocardial infarction in patients >60 years of age", *Am J Cardiol.*, 92(11), (Dec. 1, 2003), 1354-5.

(Continued)

*Primary Examiner*—Carl H Layno
*Assistant Examiner*—Paula J Stice
(74) *Attorney, Agent, or Firm*—Schwegman, Lundberg, Woessner, P.A.

(57) ABSTRACT

The health state of a subject is automatically evaluated or predicted using at least one implantable device. In varying examples, the health state is determined by sensing or receiving information about at least one physiological process having a circadian rhythm whose presence, absence, or baseline change is associated with impending disease, and comparing such rhythm to baseline circadian rhythm prediction criteria. Other chronobiological rhythms beside circadian may also be used. The baseline prediction criteria may be derived using one or more past physiological process observation of the subject or population of subjects in a non-disease health state. The prediction processing may be performed by the at least one implantable device or by an external device in communication with the implantable device. Systems and methods for invoking a therapy in response to the health state, such as to prevent or minimize the consequences of predicted impending heart failure, are also discussed.

11 Claims, 9 Drawing Sheets

U.S. PATENT DOCUMENTS

| | | | |
|---|---|---|---|
| 5,733,312 | A | 3/1998 | Schloss et al. |
| 5,749,900 | A * | 5/1998 | Schroeppel et al. ............ 607/4 |
| 5,919,209 | A | 7/1999 | Schouten |
| 6,066,163 | A * | 5/2000 | John ........................... 607/45 |
| 6,128,534 | A * | 10/2000 | Park et al. ..................... 607/17 |
| 6,272,377 | B1 | 8/2001 | Sweeney et al. |
| 6,571,122 | B2 | 5/2003 | Schroeppel et al. |
| 6,766,194 | B1 | 7/2004 | Kroll |
| 6,821,249 | B2 | 11/2004 | Casscells, III et al. |
| 6,922,587 | B2 | 7/2005 | Weinberg |
| 6,945,939 | B2 | 9/2005 | Turcott |
| 7,123,959 | B2 | 10/2006 | Cates |
| 7,194,313 | B2 | 3/2007 | Libbus |
| 7,207,947 | B2 | 4/2007 | Koh et al. |
| 2003/0055461 | A1 | 3/2003 | Girouard et al. |
| 2005/0137489 | A1 | 6/2005 | Jackson et al. |
| 2005/0143785 | A1* | 6/2005 | Libbus ........................ 607/42 |
| 2005/0149130 | A1 | 7/2005 | Libbus |
| 2005/0216067 | A1* | 9/2005 | Min et al. ..................... 607/17 |
| 2005/0234518 | A1 | 10/2005 | Heruth et al. |
| 2005/0256545 | A1 | 11/2005 | Koh et al. |
| 2006/0074451 | A1 | 4/2006 | Chen et al. |
| 2006/0122525 | A1 | 6/2006 | Shusterman |
| 2006/0270939 | A1* | 11/2006 | Wariar et al. ................ 600/528 |
| 2007/0129763 | A1 | 6/2007 | Cates |

OTHER PUBLICATIONS

Bigger, Jr., J. T., "Spectral Analysis of R-R Variability to Evaluate Autonomic Physiology and Pharmacology and to Predict Cardiovascular Outcomes in Humans", *Diagnostic Evaluation, Part XI, Chapter 101*, 1151-1170.

Ewing, D. J., et al., "Twenty four hour heart rate variability: effects of posture, sleep, and time of day in healthy controls and comparison with bedside tests of autonomic function in diabetic patients", *Br Heart J.*, 65(5), (May 1991), 239-44.

Kitzis, I., et al., "Circadian rhythm of acute pulmonary edema", *Am J Cardiol.*, 83(3), (Feb. 1, 1999), 448-50.

Manolis, A. G., et al., "Modulation of the sympathovagal balance in drug refractory dilated cardiomyopathy, treated with permanent atrioventricular sequential pacing", *Jpn Heart J.*, 41(1), (Jan. 2000), 33-40.

McMillan, D. E., et al., "Interpreting heart rate variability sleep/wake patterns in cardiac patients", *J Cardiovasc Nurs.*, 17(1), (Oct. 2002), 69-81.

Serrador, J. M., et al., "Physical activity is a major contributor to the ultra low frequency components of heart rate variability", *Heart*, 82(6), (Dec. 1999), 6 pages.

Singh, Ram B., et al., "Circadian heart rate and blood pressure variability considered for research and patient care", *International Journal of Cardiology*, vol. 87, (2003), 9-28.

Stahmann, Jeffrey E., et al., "Prediction of Thoracic Fluid Accumulation", U.S. Appl. No. 11/136,195, filed May 24, 2005, 44 Pgs.

Strand, Fleur L., "Physiology—A Regulatory Systems Approach", *Physiology a Regulatory Systems Approach, New York University, Macmillan Publishing Co., Inc.*, (1978), 617 Pages.

Zevitz, Michael E., "Heart Failure", http://www.emedicine.com/med/topic3552.htm, (Jun. 15, 2006).

PCT Application No. PCT/US2007/020425, Written Opinion mailed Apr. 28, 2008, 8 pgs.

PCT Application No. PCT/US2007/020425, International Search Report mailed Apr. 28, 2008, 5 pgs.

Faber, T. S., et al., "Beat-to-Beat Assessment of QT/RR Interval Ratio in Severe Heart Failure and Overt Myocardial Ischemia: A Measure of Electrical Integrity in Diseased Hearts", *Pacing and Clinical Electrophysiology (Pace)*, vol. 26(Apr. 2003), 836-842.

* cited by examiner

MONITORING OF CHRONOBIOLOGICAL RHYTHMS FOR DISEASE AND DRUG MANAGEMENT USING ONE OR MORE IMPLANTABLE DEVICE

TECHNICAL FIELD

This patent document pertains generally to medical systems and methods. More particularly, but not by way of limitation, this patent document pertains to monitoring of chronobiological rhythms, such as circadian rhythms, for disease and drug management using one or more implantable device.

BACKGROUND

Heart failure ("HF") is a condition in which a subject's heart can't pump the needed amount of blood to the subject's other organs causing fluid to build up behind the heart. HF is one of the leading causes of death in the United States and a leading cause of poor quality of life in the human population over the age of 65. There are currently about 5 million or more cases of HF in the United States alone, with about 1 million of them hospitalized each year. As the population of subjects 65 years of age and older grows (i.e., amid the aging of the baby boomer generation), HF threatens a dramatic increase of morbidity and mortality, along with being a burgeoning drain on healthcare funds in the United States and other countries.

Some of many needs for HF subjects is accurately predicting, monitoring, and treating heart failure decompensation before an advanced disease stage is reached. Heart failure, and more particularly heart failure decompensation, may signify the drawing near of death or, at the very least, the need for extensive hospitalization intervention. With sufficient warning, steps including drug or electrical stimulus therapy can be initiated or adjusted to save the HF subjects from either of these advanced HF consequences. Unfortunately, the time associated with typical HF detection is often too late in the disease process to prevent significant clinical intervention (e.g., hospitalization) or death.

Overview

The health state of a subject is automatically evaluated or predicted using at least one implantable device. In varying examples, the health state is determined by sensing or receiving information about at least one physiological process having a circadian rhythm whose presence, absence, or baseline change is associated with impending disease, and comparing such rhythm to baseline circadian rhythm prediction criteria. Other chronobiological rhythms beside circadian may also be used. The baseline prediction criteria may be derived using one or more past physiological process observation of the subject or population of subjects in a non-disease health state. The prediction processing may be performed by the at least one implantable device or by an external device in communication with the implantable device. Systems and methods for invoking a therapy in response to the health state, such as to prevent or minimize the consequences of predicted impending heart failure, are also discussed.

In Example 1, a system comprises a prediction criteria module, adapted to store information about one or more chronobiological rhythm prediction criteria; a physiological information collection device, adapted to sense or receive information about at least one physiological process having a chronobiological rhythm whose presence, absence, or change is statistically associated with a disease state; an impending disease state prediction module, coupled to the prediction criteria module to receive the one or more chronobiological rhythm prediction criteria and coupled to the physiological information collection device to receive the chronobiological rhythm of the at least one physiological process, the impending disease state prediction module being adapted to predict an occurrence of impending disease using the one or more chronobiological rhythm prediction criteria and the chronobiological rhythm of the at least one physiological process; and at least one of the prediction criteria module, the physiological information collection device, or the impending disease state prediction module including an implantable portion.

In Example 2, the system of Example 1 is optionally configured such that the impending disease state prediction module is adapted to predict the occurrence of impending disease during a specified prediction time period.

In Example 3, the system of Examples 1-2 is optionally configured such that the information about the at least one physiological process is sensed or received, at least in part, using an implantable device or sensor.

In Example 4, the system of Examples 1-3 is optionally configured such that the at least one physiological process includes one or more of body temperature, heart rate, heart rate variability, respiration rate, respiration rate variability, minute ventilation, tidal volume, activity, blood pressure, posture, sleep pattern, thoracic impedance, or at least one heart sound.

In Example 5, the system of Example 4 optionally includes a timing circuit coupled to the physiological information collection device to provide an associated collection time to the chronobiological rhythm of the at least one physiological process; and wherein the associated collection time is used by the impending disease state prediction module to predict the occurrence of impending disease.

In Example 6, the system of Examples 1-5 optionally includes an arrhythmia detector adapted to sense or receive information about an arrhythmia incidence; and wherein a time of the arrhythmia incidence is used by the impending disease state prediction module to predict the occurrence of impending disease.

In Example 7, the system of Examples 1-6 is optionally configured such that the predicted occurrence of impending disease is computed using one or more stored weighting factor, each weighting factor corresponding to a chronobiological rhythm of a different one of the at least one physiological process.

In Example 8, the system of Examples 1-7 is optionally configured such that the chronobiological rhythm prediction criteria are derived using one or more past physiological process observation from a subject in a non-disease state.

In Example 9, the system of Examples 1-8 optionally includes a therapy control module adapted to adjust or initiate a therapy using the predicted occurrence of impending disease.

In Example 10, the system of Example 9 optionally includes an implantable drug pump, coupled to the therapy control module to receive one or more drug delivery instruction.

In Example 11, the system of Example 9 optionally includes a neural stimulation circuit, coupled to the therapy control module to receive one or more neurostimulation delivery instruction.

In Example 12, the system of Example 9 optionally includes at least one of a ventricular or atrial stimulation circuit, coupled to the therapy control module to receive one or more cardiac stimulation delivery instruction.

In Example 13, a method comprises sensing or receiving at an implantable device, information about at least one physiological process having a chronobiological rhythm whose presence, absence, or change is statistically associated with a disease; comparing the chronobiological rhythm of the at least one physiological process to one or more chronobiological rhythm prediction criteria; and at least one of predicting, detecting, or identifying an occurrence of disease using the comparison.

In Example 14, the method of Example 13 is optionally configured such that predicting the occurrence of disease includes predicting an occurrence of impending disease occurring during a specified prediction time period.

In Example 15, the method of Examples 13-14 is optionally configured such that sensing or receiving the information about the at least one physiological process includes sensing or receiving at least one of body temperature, heart rate, heart rate variability, respiration rate, respiration rate variability, minute ventilation, tidal volume, activity, blood pressure, posture, sleep pattern, thoracic impedance, or at least one heart sound.

In Example 16, the method of Examples 13-15 optionally includes sensing or receiving information about at least one arrhythmia incidence; and wherein predicting the occurrence of disease includes using a time of day of the arrhythmia incidence.

In Example 17, the method of Examples 13-16 optionally includes adjusting or initiating a therapy using the predicted, detected, or identified occurrence of disease.

In Example 18, the method of Example 17 is optionally configured such that adjusting or initiating the therapy includes determining a drug delivery time using the chronobiological rhythm of the at least one physiological process.

In Example 19, the method of Example 17 is optionally configured such that adjusting or initiating the therapy includes recovering the chronobiological rhythm of the at least one physiological process using one or both of drug delivery or neurostimulation.

In Example 20, the method of Example 17 optionally includes monitoring the efficacy of the therapy using a post-therapy chronobiological rhythm of the at least one physiological process.

In Example 21, a method comprises sensing or receiving at an implantable device, information about at least one physiological process having a chronobiological rhythm whose presence, absence, or change is statistically associated with a disease; comparing the chronobiological rhythm of the at least one physiological process to one or more chronobiological rhythm prediction criteria; and applying a therapy.

In Example 22, the method of Example 21 is optionally configured such that applying the therapy includes using the comparison of the chronobiological rhythm and the one or more chronobiological rhythm prediction criteria.

In Example 23, the method of Examples 21-22 is optionally configured such that applying the therapy includes using a subject-responsive drug delivery time derived using one or more past post-therapy chronobiological rhythm observations from a subject in a similar pre-therapy disease-state.

In Example 24, the method of Examples 21-23 optionally includes monitoring the efficacy of the therapy using a post-therapy chronobiological rhythm of the at least one physiological process.

In Example 25, a method comprises applying a therapy to a subject; and monitoring the efficacy of the therapy, including sensing or receiving at an implantable device a post-therapy chronobiological rhythm associated with at least one of body temperature, heart rate, heart rate variability, respiration rate, respiration rate variability, minute ventilation, tidal volume, activity, blood pressure, posture, sleep pattern, thoracic impedance, or at least one heart sound.

In Example 26, the method of Example 25 is optionally configured such that applying the therapy includes delivering one or both of drug or electrical stimulation therapy to the subject.

In Example 27, the method of Examples 25-26 optionally includes titrating the therapy using the monitored efficacy of the therapy.

BRIEF DESCRIPTION OF THE DRAWINGS

In the drawings, which are not necessarily drawn to scale, like numerals describe substantially similar components throughout the several views. The drawings illustrate generally, by way of example, but not by way of limitation, various embodiments discussed in the present document.

DETAILED DESCRIPTION

Figure 1:
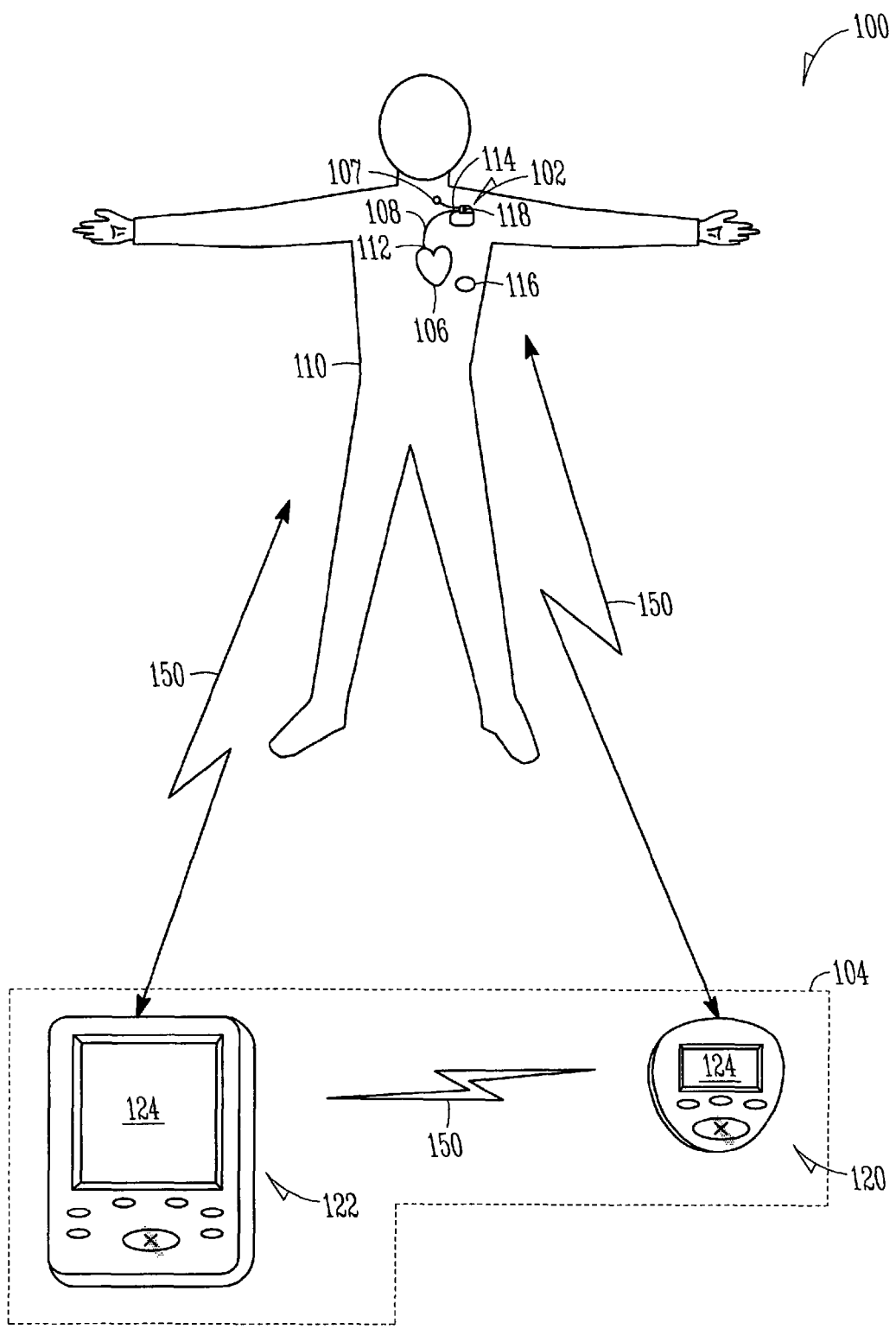
FIG. 1 is a schematic view illustrating a system adapted to predict, monitor, or treat an occurrence of impending heart failure or other disease state in a subject.

The following detailed description includes references to the accompanying drawings, which form a part of the detailed description. The drawings show, by way of illustration, specific embodiments in which the present systems and methods may be practiced. These embodiments, which are also referred to herein as "examples," are described in enough detail to enable those skilled in the art to practice the present systems and methods. The embodiments may be combined, other embodiments may be utilized or structural, electrical, or logical changes may be made without departing from the scope of the present systems and methods. The following detailed description is, therefore, not to be taken in a limiting sense, and the scope of the present systems and methods are defined by the appended claims and their legal equivalents.

In this document, the terms "a" or "an" are used to include one or more than one; the term "or" is used to refer to a nonexclusive "or" unless otherwise indicated; the term "subject" is used to include the term "patient"; and the terms "predict," "prediction," or other variants thereof are used to denote a probability assertion or statement regarding whether or not an occurrence of impending heart failure or other disease state might occur during a specified time period. In addition, it is to be understood that the phraseology or terminology employed herein, and not otherwise defined, is for the purpose of description only and not of limitation.

Furthermore, all patents and patent documents referred to in this document are incorporated by reference herein in their entirety, as though individually incorporated by reference. In the event of inconsistent usages between this document and those documents so incorporated by reference, the usage in the incorporated references should be considered supplementary to that of this document; for irreconcilable inconsistencies, the usage in this document controls.

Introduction

HF and other disease states are associated with a loss or baseline change of one or more circadian rhythms, especially when the subject decompensates. A subject's body, when relatively healthy (i.e., in a non-disease state), has more than 100 circadian rhythms. Each circadian rhythm is a unique, roughly 24-hour cycle of a subject's physiological process, such as body temperature (core or peripheral), heart rate, heart rate variability, respiration rate, respiration rate variability, minute ventilation, activity, blood pressure, posture, tidal volume, sleep quality or duration, thoracic impedance, or heart sounds, among others.

The present systems and methods may predict, monitor, or treat an impending disease state of a subject, such as the likelihood of an occurrence of heart failure, using circadian or other rhythm monitoring. In certain examples, treating the impending disease state of the subject includes adjusting or initiating one or more therapies (e.g., drug therapy or neurostimulation), such as to prevent, decrease, or minimize such predicted impending disease state or monitor the efficacy of such applied therapy. In certain examples, monitoring the impending disease state of the subject includes monitoring the subject's recovery from the impending disease state in light of the applied therapy.

As will be discussed below, the prediction, monitoring, or treatment of an impending disease state can be made by sensing or receiving one or more circadian (or other chronobiological) rhythms associated with a subject's physiological process and by comparing such rhythm(s) to one or more baseline chronobiological rhythm prediction criteria that are derived by a caregiver (e.g., a physician) or from at least one subject in a non-disease state. Advantageously, prediction, monitoring, or treatment of an impending disease state, such as heart failure, may reduce or eliminate the need for hospital intervention, and may be useful for avoiding a decompensation crisis and properly managing a heart failure subject in a state of relative well-being.

EXAMPLES

The techniques of the present systems and methods may be used in applications involving implantable medical devices ("IMDs") including, but not limited to, implantable cardiac rhythm management ("CRM") systems such as pacemakers, cardioverters/defibrillators, pacemakers/defibrillators, biventricular or other multi-site resynchronization or coordination devices such as cardiac resynchronization therapy ("CRT") devices, patient monitoring systems, neural modulation systems, and drug delivery systems. In addition, the systems and methods described herein may also be employed in unimplanted devices, including but not limited to, external pacemakers, neutral stimulators, cardioverters/defibrillators, pacer/defibrillators, biventricular or other multi-site resynchronization or coordination devices, monitors, programmers and recorders, whether such devices are used for providing sensing, receiving, prediction processing, or therapy.

FIG. 1 is a schematic view illustrating one example of a system 100 adapted to predict, monitor, or treat an occurrence of impending heart failure or other disease state in a subject 110 using sensed or received information about at least one physiological process having a circadian rhythm whose presence, absence, or baseline change is statistically associated with a disease state, and an environment in which the system 100 may be used. As shown in FIG. 1, the system 100 may include an IMD 102, such as a CRM device, which can be coupled by at least one lead 108 to a heart 106 or efferent parasympathetic nerve, such as a vagus nerve 107, of the subject 110. The IMD 102 may be implanted subcutaneously in the subject's chest, abdomen, or elsewhere. Each of the at least one lead 108 extends from a lead proximal portion 114 to a lead distal portion 112.

The exemplary system 100 also includes a physiological information collection device 104, remote portions (e.g., a nearby external user-interface 120 or a distant external user interface 122) of which are shown in FIG. 1, a drug delivery system (e.g., a drug pump 116), and a warning device 118. The remote portions 120, 122 of the physiological information collection device 104 may provide wireless communication with the IMD 102 and with one another using telemetry 150 or other known communication techniques. In one example, the prediction, monitoring, or treatment of the occurrence of impending heart failure or other disease state is made, at least in part, by receiving information about at least one physiological process having a circadian rhythm remotely (e.g., at the nearby 120 or distant 122 external user interface) and then communicating signals representative of the circadian rhythm, or lack thereof, to the IMD 102 for processing. In certain examples, the remote portions of the physiological information collection device 104 include a visual or other display 124, such as a LCD or LED display, for textually or graphically relaying information to the subject 110 or a caregiver regarding operation, findings (e.g., loss or baseline change of one or more circadian rhythms; recovery of the one or more circadian rhythms), or predictions of the system 100.

The drug pump 116 or another drug dispensing device may be provided in addition to the IMD 102 to control the delivering of one or more therapy drug to the subject 110 or, if already doing so, to adjust or terminate a dosage of the delivered drug(s). The efficacy of the drug therapy may be evaluated based on changes, if any, in the circadian rhythms of the at least one physiological process sensed or received by the physiological information collection device 104. For instance, if the system 100 initially detects a loss or baseline change of one or more of a subject's circadian rhythms (e.g., relative to one or more baseline circadian rhythm prediction criteria) and thereafter directs the drug pump 116 to deliver a diuretic or other drug in an attempt to regain normal (or non-disease like) circadian rhythm(s), the efficacy of such diuretic drug therapy and the subject's 110 recovery state may be evaluated by monitoring post-therapy circadian rhythm(s) of at least one physiological process. In a similar manner, the efficacy of electrical stimulation therapy, such as neurostimulation therapy, may be evaluated.

If the system 100, based on circadian rhythm monitoring, comes to the conclusion that an occurrence of heart failure (for example) is likely to occur during a predicted future time period for the subject 110, one or more warning signals may be made to the subject or his/her caregiver. Warning signals may be generated using either an internal warning device 118 or the external user interfaces 120, 122 so-as-to notify the subject 110 or his/her caregiver of the onset of heart failure or other disease state. The internal warning device 118 may be a vibrating or audible device that provides perceptible stimulation to the subject 110 to alert him/her of any significant progression of heart failure so that he/she may immediately consult their caregiver. The external user interfaces 120, 122 may provide audible alarm signals to alert the subject 110 as well textual or graphic displays. In addition, once impending heart failure has been predicted by the system 100, information used to make the prediction (e.g., loss of one or more circadian rhythms) is stored within the IMD 102 or sent to the distant external user interface 122 for review by the caregiver. If warranted, the caregiver may then initiate or modify a (stimulation or drug) therapy or adjust control parameters of the IMD 102 or drug pump 116.

Figure 2:
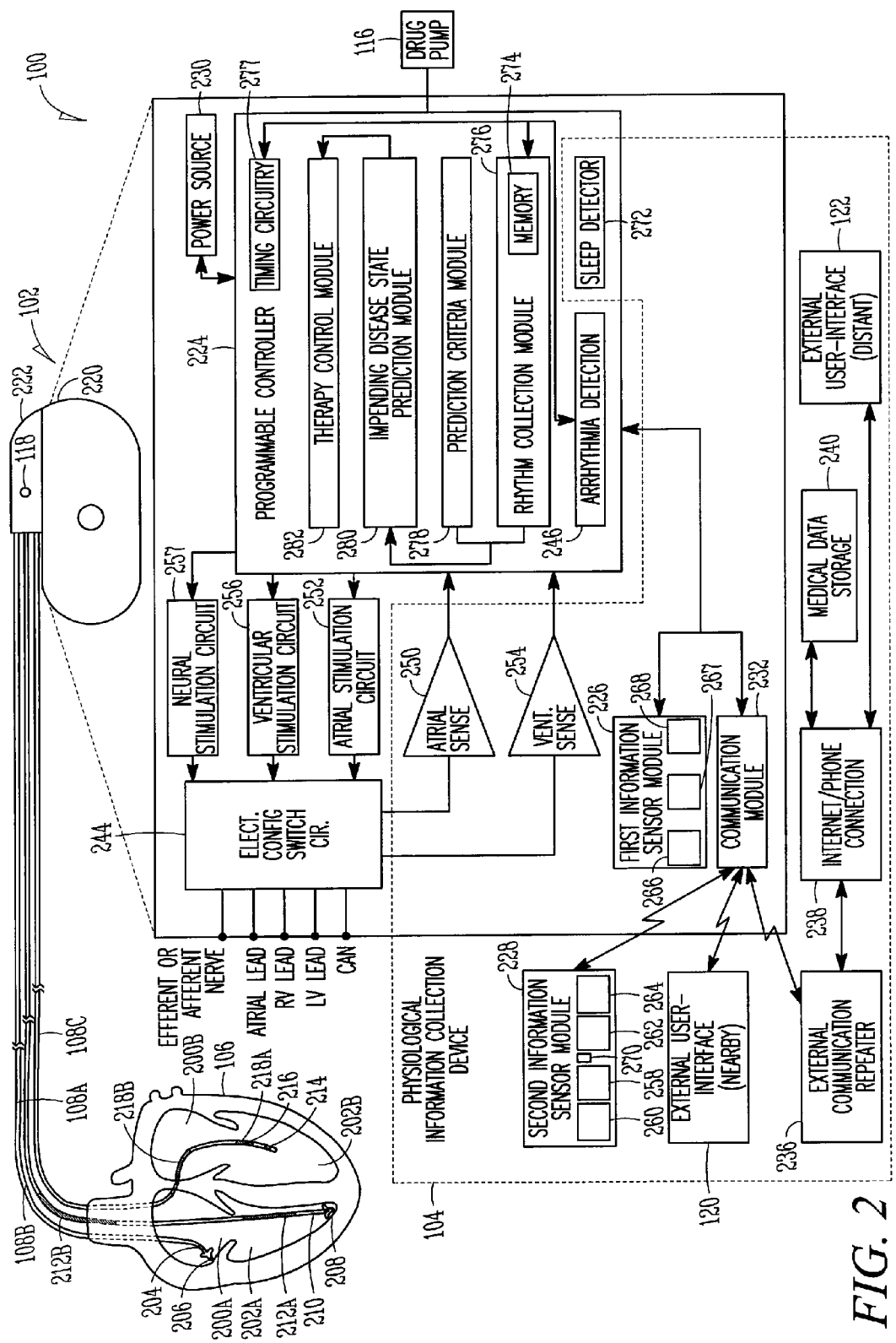
FIG. 2 is a block diagram illustrating one conceptual example of a system adapted to predict, monitor, or treat an occurrence of impending heart failure or other disease state in a subject.

FIG. 2 provides a simplified block diagram illustrating one conceptual example of a system 100 adapted to predict, monitor, or treat an occurrence of impending heart failure or other disease state in a subject 110 (FIG. 1). In certain examples, treating the impending HF or other disease state includes adjusting or initiating one or more therapies, such as electrical stimulation or drug therapy. In certain examples, monitoring the impending HF or other disease state includes monitoring the subject's 110 recovery from the impending disease in light of the applied therapy.

FIG. 2 further illustrates an exemplary placement of a plurality of leads 108A, 108B, 108C, specifically lead distal end portions, within, on, or near a heart 106 of the subject 110. As shown, the heart 106 includes (among other things) a right atrium 200A, a left atrium 200B, a right ventricle 202A, and a left ventricle 202B. In this example, an atrial lead 108A includes electrodes disposed in, around, or near the right atrium 200A of the heart 106, such as a ring electrode 204 and a tip electrode 206, for sensing signals (e.g., via atrial sensing circuit 250) or delivering pacing or other stimulation therapy (e.g., via atrial stimulation circuit 252) to the right atrium 200A. The atrial lead 108A may also include additional electrodes, such as for delivering atrial or ventricular cardioversion/defibrillation or pacing therapy to the heart 106.

In FIG. 2, a right ventricular lead 108B is also shown and includes one or more electrodes, such as a tip electrode 208 and a ring electrode 210, for sensing signals (e.g., via ventricular sensing circuit 254) or delivering pacing or other stimulation therapy (e.g., via ventricular stimulation circuit 256). The right ventricular lead 108B may also include additional electrodes, such as one or more coil electrode 212A or 212B for delivering atrial or ventricular cardioversion/defibrillation or pacing therapy to the heart 106. Further, the system 100 of FIG. 2 also includes a left ventricular lead 108C, which provides one or more electrodes such as a tip electrode 214 and a ring electrode 216, for sensing signals or delivering pacing or other stimulation therapy. The left ventricular lead 108C may also include one or more additional electrodes, such as coil electrodes 218A or 218B for delivering atrial or ventricular cardioversion/defibrillation or pacing therapy to the heart 106.

As shown, the IMD 102 includes electronic circuitry components that are enclosed in a hermetically-sealed enclosure, such as a can 220. Additional electrodes may be located on or near an efferent parasympathetic or afferent nerve, on the can 220, on an insulating header 222, or on other portions of the IMD 102, such as for sensing or for providing neurostimulation, pacing, or defibrillation energy, for example, with or without the electrodes disposed within, on, or near the heart 106. Other forms of electrodes include meshes and patches that may be applied to portions of the heart 106 or that may be implanted in other areas of the body to help direct electrical currents produced by the IMD 102. For example, a warning electrode 118 on the insulating header 222 may be used to stimulate local muscle tissue to provide an alert/warning of a prediction of impending disease to the subject 110. The present systems and methods are adapted to work in a variety of electrode configurations and with a variety of electrical contacts or electrodes in addition to the electrode configuration shown in FIG. 2.

It is to be noted that FIG. 2 illustrates just one conceptualization of various modules, circuits, and interfaces of system 100, which are implemented either in hardware or as one or more sequences of steps carried out on a microprocessor or other controller. Such modules, devices, and interfaces are illustrated separately for conceptual clarity; however, it is to be understood that the various modules, devices, and interfaces of FIG. 2 need not be separately embodied, but may be combined or otherwise implemented. The IMD 102, in particular, may be powered by a power source 230, such as a battery, which provides operating power to all the IMD internal modules and circuits shown in FIG. 2. In certain examples, the power source 230 should be capable of operating at low current drains for long periods of time and also be capable of providing high-current pulses (for capacitor charging) when the subject 110 (FIG. 1) requires a shock pulse.

In this example, the system 100 further includes a physiological information collection device 104 adapted to sense or receive information about at least one physiological process having a circadian rhythm whose presence, absence, or baseline change is statistically associated with a disease state. In varying examples, the at least one physiological process includes one or more of body temperature (core or peripheral), heart rate, heart rate variability, respiration rate, respiration rate variability, minute ventilation, activity, blood pressure, posture, tidal volume, sleep quality or duration, thoracic impedance, or heart sounds. Circadian rhythm representative signals associated with the at least one physiological process may be output to a programmable controller 224 for performing the prediction, monitoring, or treatment of the occurrence of impending heart failure or other disease state. Additionally or alternatively, a time of the circadian rhythm representative signal collection, a clinical event, or an arrhythmia incidence (atrial or ventricular) may be output to the programmable controller 224 and used in the prediction, monitoring, or treatment. For instance, it has been found that certain diseases, such as pulmonary edema, tend to disrupt (i.e., lose or change from baseline) at least one physiological process's circadian rhythm at certain times of a day or week. Using such information, one (e.g., a caregiver or the IMD 102 itself) can more easily treat the impending disease.

As shown, the physiological information collection device 104 may include an atrial sensing circuit 250, a ventricular sensing circuit 254, a first information sensor module 226, a second information sensor module 228, a communication module 232, a (nearby) external user interface 120 (e.g., a home station device), an external communication repeater 236, an Internet or other communication network connection 238, a computerized medical data storage 240, or a (distant) external user interface 122 (e.g., a physician station device).

The atrial 250 and ventricular 254 sensing circuits, the first information sensor module 226, and the communication module 232 may be directly coupled to the programmable controller 224; while the second information sensor module 228, the (nearby) external user interface 120, and the external communication repeater 236 may be communicatively coupled with the communication module 232 via telemetry, and thus also be in communication with the programmable controller 224. In this example, the communication module 232 is capable of wirelessly communicating with the computerized medical data storage 240 or the (distant) external user interface 122, such as by using the external communication repeater 236 and the Internet/phone connection 238. In one example, the nearby 120 or distant 122 external user interface controls, loads, or retrieves information from the IMD 102, and is adapted to process and display (e.g., textually or graphically) such information obtained.

The atrial 250 and ventricular 254 sensing circuits may be selectively coupled to the atrial lead 108A, the right ventricular lead 108B, or the left ventricular lead 108C, via an electrode configuration switching circuit 244, for detecting the presence of intrinsic cardiac activity in each of the four chambers of the heart 106. These intrinsic heart activity signals typically include depolarizations that propagate through the circulatory system. The depolarizations cause heart contractions for pumping blood through the circulatory system. The atrial 250 and ventricular 254 sensing circuits may include dedicated sense amplifiers, multiplexed amplifiers, shared amplifiers, or other signal processing circuits to extract depolarizations or other useful information from the intrinsic heart activity signals. For instance, each of the atrial 250 or ventricular 254 sensing circuits may employ one or more low power, precision amplifier with programmable or automatic gain, bandpass filtering, or a threshold detection circuit, to selectively sense the cardiac signal of interest.

For arrhythmia detection 246, the IMD 102 utilizes the atrial 250 and ventricular 254 sensing circuits to sense cardiac signals for determining whether a rhythm is normal or pathologic.

For thoracic impedance detection, the IMD 102 may inject an electrical stimulus current of known or attainable value (e.g., via the ventricular 256 or atrial 252 stimulation circuits) to one or more implanted electrodes and measure (e.g., via the ventricular 254 or atrial 250 sense circuits) the resulting voltage using one or more other implanted electrodes. Using information about the current and the resulting voltage, the IMD 102 may calculate an impedance by taking a ratio of resulting voltage to injected current. This measurement may be repeated over time to detect changes in impedance (and thus changes in fluid amount in the lungs). A reduction in thoracic impedance indicates the presence of an increase in fluid within the lungs. Conversely, a fluid decrease in the lungs corresponds to an increase in thoracic impedance sensed.

In FIG. 2, the first 226 and second 228 information sensor modules include one or more physiologic process sensors, such as a temperature sensor 260, a blood pressure sensor 258, a respiratory rate/respiratory rate variability sensor 262, a tidal volume/MV sensor 264, an activity sensor 270, a heart rate/heart rate variability sensor 266, a posture sensor 268, or an accelerometer or microphone 267. In one example, each information sensor module 226, 228 also includes one or more interface circuits that receive one or more control signals and preprocesses the sensor signal(s) received. In another example, the first 226 and second 228 information sensor modules are combined as a single module.

A sleep detector 272 shown associated with the programmable controller 224 inputs signals from the various physiological information sensors 258-270 or the nearby external user interface 120 to determine whether the subject 110 is in a state of sleep, and if so, determines the quality of such sleep. In some examples, the programmable controller 224 determines whether the subject 110 is attempting to fall asleep based on whether the subject is or is not in a recumbent position, determinable via the posture sensor 268. In some examples, a sleep state detection system, such as described in Dalal et al., U.S. patent application Ser. No. 11/458,602 entitled, "SLEEP STATE DETECTION," which is assigned to Cardiac Pacemakers, Inc., is used to determine whether or not the subject 110 is in a state of sleep.

Other ways in which the programmable controller 224 may identify when the subject 110 (FIG. 1) is attempting to sleep are as follows. In one example, the programmable controller 224 may identify the time that the subject 110 begins attempting to fall asleep based on an indication received from the subject, such as via nearby external user interface 120 and the communication module 232. In another example, the programmable controller 224 identifies the time the subject 110 begins attempting to fall asleep based on the activity level of the subject determined via the activity sensor 270. The activity sensor 270 may include one or more accelerometers, gyros, or bonded piezoelectric crystals that generate a signal as a function of subject activity pattern, such as body motion, foot strikes or other impact events, and the like. Additionally or alternatively, the activity sensor 270 may include one or more electrodes that generate an electromyogram ("EMG") signal as a function of muscle electrical activity, which may indicate the activity level of the subject 110. The electrodes may, for example, be located in the legs, abdomen, cheek, back, or buttocks of the subject 110 to detect muscle activity associated with walking, running, or the like.

The programmable controller 224 includes various functional modules, circuits, and detectors, one conceptualization of which is illustrated in FIG. 2. Among other things, the programmable controller 224 may include control circuitry, a RAM or ROM memory 274, logic and timing circuitry 277 to keep track of the timing of sensing or receiving circadian rhythm representative signals associated with physiological processes of the subject 110 (FIG. 1), for example, and I/O circuitry. Additionally, the programmable controller 224 may include a rhythm collection module 276 that receives from the physiological information collection device 104 information about the at least one physiological process having a circadian rhythm whose presence, absence, or baseline change is associated with a disease state. The rhythm collection module 276 may include the memory 274 to store signals representative of such circadian rhythm(s) and may further classify such rhythm(s) as being associated with one or more of body temperature (core or peripheral), heart rate, heart rate variability, respiration rate, respiration rate variability, minute ventilation, activity, blood pressure, posture, tidal volume, sleep quality or duration, thoracic impedance, or heart sounds.

In this example, the programmable controller 224 also includes a prediction criteria module 278 adapted to store one or more baseline circadian rhythm prediction criteria. In one example, the one or more baseline circadian rhythm prediction criteria are derived using one or more past physiological process observation of the subject when in a non-disease health state (i.e., in a relatively healthy state). In another example, the one or more baseline circadian rhythm prediction criteria are derived using one or more past physiological process observation of a population when in a non-disease health state. In a further example, the one or more baseline circadian rhythm prediction criteria are loaded into the IMD 102 before, during, or after the IMD 102 is implanted in the subject 110, such as via an external user-interface 120, 122.

For predicting, monitoring, or treating the occurrence of impending heart failure or other disease state, the programmable controller 224 includes an impending disease state prediction module 280 and a therapy control module 282. The impending disease state prediction module 280 is coupled to both the prediction criteria module 278 to receive the one or more baseline circadian rhythm prediction criteria, and is coupled to the physiological information collection device 104 (via the rhythm collection module 276) to receive the circadian rhythm representative signals associated with the at least one physiological process. The impending disease state prediction module 280 predicts the likelihood of future heart failure, for example, using the one or more baseline circadian rhythm prediction criteria and the circadian rhythm representative signals associated with the at least one physiological process sensed or received. More specifically, the impending disease state prediction module 280 predicts the likelihood of impending heart failure based on a determination of whether or not the circadian rhythm(s) of the at least one physiological process have been lost or changed (e.g., relative to the baseline circadian rhythm prediction criteria).

The therapy control module 282 is programmed to select (from a set of available therapies) the most appropriate responsive therapy (or combination of therapies), such as for reducing the likelihood or even preventing the predicted occurrence of impending disease (e.g., heart failure). In one example, the therapy control module 282 also triggers the delivery of the selected therapy after determining if the probability of the occurrence of impending disease state, computed by the impending disease state prediction module 280, warrants such administration.

In one example, such therapy is provided via electrodes associated with the heart 106 or portions of a subject's nervous system such as, for example, sympathetic or parasympathetic members of the autonomic nervous system. In one such example, the electrodes provide neurostimulation via a neural stimulation circuit 257 in electrical contact with the vagus nerve 107 (FIG. 1) or a baroreceptor, thereby adjusting autonomic tone to restore tone indicative of normal circadian rhythm. The vagus nerve 107 provides parasympathetic stimulation to the heart 106 (FIG. 1) that counteracts the effects of increased sympathetic activity, and stimulation of the vagus nerve 107 at either a pre-ganglionic or post-ganglionic site produces dilation of the coronary arteries and a reduced workload on the heart 106. Baroreceptors are sensory nerve endings located in the heart 106 and vasculature that are stimulated by increased fluid pressure. Stimulation of baroreceptors causes impulses to be relayed via afferent pathways to nuclei in the brainstem that result in parasympathetic activation and sympathetic inhibition.

A subject's 110 autonomic balance may vary in accordance with circadian rhythms. To this end, the neural stimulation circuit 257 (via the therapy control module 282) may be programmed to schedule delivery of neurostimulation in accordance with the subject's circadian rhythms for increased beneficial effect. The neural stimulation circuit 257 (via the therapy control module 282) may be programmed to titrate the delivery of neurostimulation by scheduling such delivery or adjusting the level of the neurostimulation in an open- or closed-loop manner that takes into consideration the effects of the circadian rhythm representative signals sensed or received.

In another example, such therapy is provided elsewhere (e.g., communicated to nearby external user interface 120 or delivered via a drug pump 116 (FIG. 1)) and includes, for example, a drug dose, a diet regimen, or a fluid intake regimen. In either case, the programmable controller 224 may control the therapy provided in view of any detected recovery or further loss or change of the subject's circadian rhythms. For instance, the programmable controller 224 may direct that therapy be increased if the subject's circadian rhythms are being further lost relative to the baseline prediction criteria or that the therapy be decreased or terminated if the subject's circadian rhythms are being recovered (i.e., regained). Further yet, the programmable controller 224 may be used to determine the efficacy of any drug or other therapy administered to the subject 110, such as via drug pump 116.

Moreover, the programmable controller 224, specifically the therapy control module 282, can use knowledge of the subject's 110 (FIG. 1) circadian rhythms to determine (1) the time when the subject needs a therapy the most or (2) the time when the subject is most responsive to the therapy (i.e., a subject-responsive drug delivery time), and then deliver the therapy as such. For instance, in a preclinical study, it was found that thoracic impedance followed a pattern of low evening/night time impedance (indicative of more fluid in the subject) followed by an increasing day time-afternoon impedance (indicative of less fluid in the subject). Thus, when a specimen was given diuretics during the day, a greater effect was observed than when diuretics were given during the late evening. Consequently, such information can be used to direct the consumption of diuretics or other drugs during the day due to its greater observed effect. Alternatively or additionally, this knowledge may be used to determine an expected drug effect give the time of day it is administered.

Nearby 120 and distant 122 external user-interfaces may be used in, among other things, programming the IMD 102. Briefly, the user-interfaces permit a caregiver or other user to program the operation of the IMD 102 or to retrieve and display information (e.g., textually or graphically) received from the IMD 102. Depending upon the specific programming of the external user-interfaces 120, 122, each interface may also be capable of processing and analyzing data received from the IMD 102 and, for example, render an impending disease state prediction.

Figure 3:
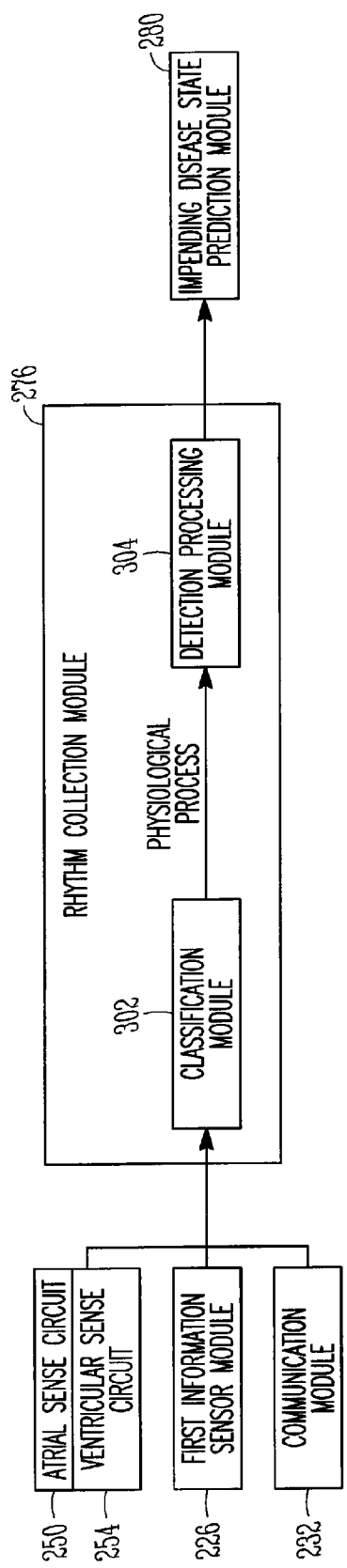
FIG. 3 is a block diagram illustrating one conceptual example of a rhythm collection module.

FIG. 3 is a block diagram illustrating one conceptual example of a portion of a rhythm collection module 276. In one example, the rhythm collection module 276 includes a classification module 302 and a detection processing module 304. In such an example, the rhythm collection module 276 is programmed to recurrently receive, store, and detect the presence, time (via timing circuitry 277), and magnitude of the circadian rhythm representative signals associated with at least one physiological process sensed or received by the atrial sensing circuit 250, the ventricular sensing circuit 254, the first information sensor module 226, or the communication module 232 (communicatively coupled to the second information module 228, the (nearby) external user interface 120, and the external communication repeater 236). The classification module 302 separates the received circadian rhythm representative signals into one or more associated physiological process categories, such as body temperature (core or peripheral), heart rate, heart rate variability, respiration rate, respiration rate variability, minute ventilation, activity, blood pressure, posture, tidal volume, sleep quality or duration, thoracic impedance, or heart sounds. The classified circadian rhythm representative signals are then output to the detection processing module 304, which is adapted to detect the presence, time, or magnitude of the signals received. From the rhythm collection device 276, the circadian rhythm representative signals are output to an impending disease state prediction module 280.

Figure 4:
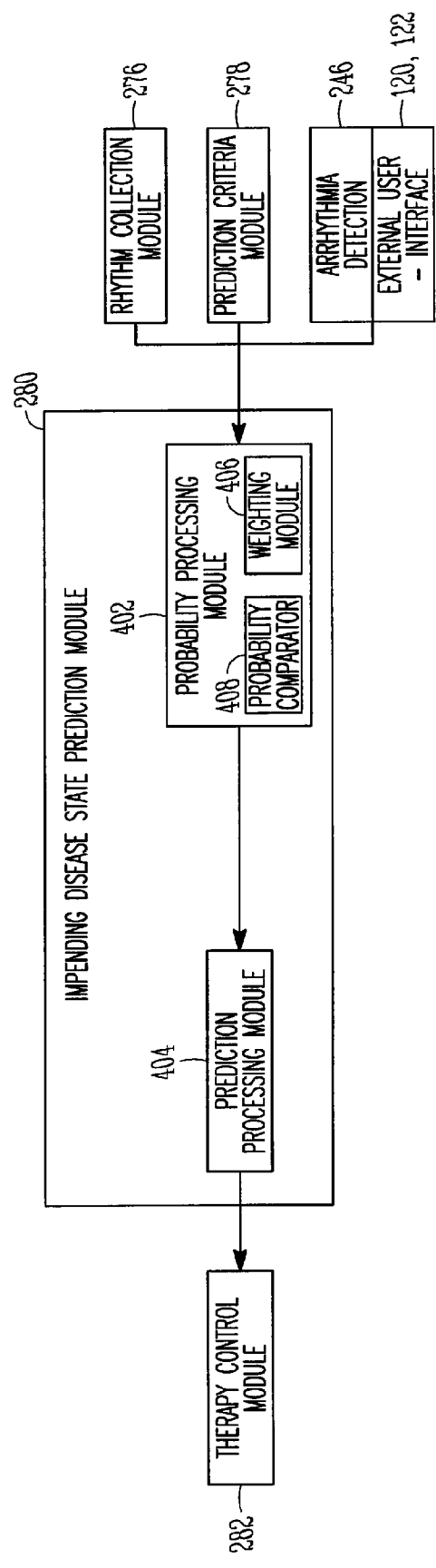
FIG. 4 is a block diagram illustrating one conceptual example of an impending disease state prediction module.

FIG. 4 is a block diagram illustrating one conceptual example of a portion of an impending disease state prediction module 280. In one example, the impending disease state prediction module 280 includes a probability processing module 402 and a prediction processing module 404. The impending disease state prediction module 280 includes an input that receives the at least one circadian rhythm representative signal ($S_1, S_2, \ldots, S_N$) from the rhythm collection module 276 and includes an input that receives the baseline circadian rhythm prediction criteria from the prediction criteria module 278. Optionally, the impending disease state prediction module 280 includes an input that receives from an arrhythmia detector 246 or an external user-interface 120, 122 a time of day of an arrhythmia incident or a clinical event.

In one example, the probability processing module 402 includes a weighting module 406 and a probability comparator 408. After entering the impending disease state prediction module 280, the at least one circadian rhythm representative signal ($S_1, S_2, \ldots, S_N$) and the baseline circadian rhythm prediction criteria are received by the probability processing module 402. The probability comparator 408 compares one or more circadian rhythm representative signal ($S_1, S_2, \ldots, S_N$) value to one or more corresponding baseline circadian rhythm prediction criteria ($C_1, C_2, \ldots, C_N$) value, such as one or more value sensed at a similar time of day and associated with the same physiological process. In another example, the at least one circadian rhythm representative signal ($S_1, S_2, \ldots, S_N$) is analyzed with respect to at least one other circadian rhythm representative signal associated with the same physiological process.

Data analysis and comparison of sensed or received circadian rhythms may involve both graphical and numerical procedures, and may further be characterized by one or more of a mean/median level, an amplitude, a phase, a period, a wave form, or robustness, for example. For instance, data analysis and comparison techniques that may be used in the prediction of an occurrence of impending disease include, among others, spectral analysis such as a strength or width of the circadian peak of the rhythm spectrum, 24-hour synchronous averaging, day/night differences, daily minimum/maximum differences, order statistics such as upper-quartile vs. lower quartile differences, phase lag/drift/stability with respect to a 24-hour clock, or wake/sleep differences.

In one example, for each circadian rhythm representative signal ($S_1, S_2, \ldots, S_N$) value or set of chronological circadian rhythm values differing by more than a specified amount from the baseline prediction criteria ($C_1, C_2, \ldots, C_N$) value or set of values, indicating a loss of circadian rhythm, the probability comparator 408 summarizes (e.g., via logistic regression) and outputs to the prediction processing module 404 a probability indication of the occurrence of impending disease, such as heart failure. The comparisons may be discrete or continuous.

In another example, the weighting module 406 stores weighting factors ($Weight_1, Weight_2, \ldots, Weight_N$), wherein each weighting factor corresponds to a different one of the circadian rhythm representative signals received by the probability processing module 402 (i.e., each weighting factor corresponds to a different physiological process sensed or received). Weighting factors may be used for computing the probability indication of the occurrence of an impending disease state, such as heart failure, by providing a degree to which each physiological process's circadian rhythm enters into the probability indication. In one example, each weight ($Weight_1, Weight_2, \ldots, Weight_N$) is computed using historical data relating the corresponding circadian rhythm of the physiological process sensed or received to the occurrence of impending heart failure, for example. In one such example, the historical data is obtained from the same subject 110 from whom the circadian rhythm information of the physiological process is sensed or received. In another such example, the historical data is obtained from at least one different subject than the circadian rhythm information (i.e., the circadian rhythm representative signal(s)) was obtained from. In a further such example, the historical data is obtained from a population of subjects.

Each weight may be computed using not only information about which physiological process the circadian rhythm is associated with, but may be computed using information about which other or how many other physiological process(es)' circadian rhythms also being used to predict the occurrence of impending heart failure or other disease state. As an illustrative example, suppose sensed or received circadian rhythms A and B each have weights of 0.1, leading to a combined prediction weight of 0.2. In another example, however, the circadian rhythms A and B each have weights of 0.1 when these rhythms are individually used to predict the occurrence of impending disease, but have a different (e.g., greater or lesser) weight when both are present (e.g., stronger weights of 0.5 when both A and B are sufficiently present and used to predict the occurrence of impending disease). That is, the weight values may depend on cross-correlation between two or more circadian rhythms. In a further example, a weight value depends on how many circadian rhythms are being used to compute the predicted occurrence of impending disease. As an illustrative example, suppose circadian rhythm A has a weight of 0.5 when it is used alone for predicting the occurrence of impending heart failure decompensation. In another example, however, circadian rhythm A has a weight of 0.25 when used in combination with one other circadian rhythm associated with a different physiological process (e.g., circadian rhythm B or circadian rhythm C, etc.).

In one example, the prediction processing module 404 generates, using the probability indication output from the probability processing module 402, a probability assertion or statement that an occurrence of impending disease will occur during a specified period after the prediction. An example of such a probability assertion or statement is a 50% probability that an occurrence of impending heart failure decompensation will occur during 5 days of the prediction generation. This assertion or statement of prediction includes both a magnitude (50%) and a well defined time period during which the prediction is applicable (5 days).

Impending disease state prediction module 280 outputs an impending disease state prediction to a therapy control module 282, which in turn bases control of preventive or other therapy on the disease state prediction. In one example, as discussed above, the impending disease state prediction output from the impending disease state prediction module 280, more particularly the prediction processing module 404, includes a set of one or more probability assertions or statements. Each probability statement includes both a magnitude of the probability (e.g., a 50% probability of impending heart failure decompensation exists) and a specified future time period associated therewith (e.g., will occur within 5 days). In another example, each probability statement also identifies which circadian rhythm representative signal(s), and thus which physiological process, contributed to its magnitude.

In an alternative example, the impending disease state prediction calculation and output from the impending disease state prediction module 280 takes the form of a conditional probability computation, such as described in Sweeney et al., U.S. Pat. No. 6,272,377 entitled, "CARDIAC RHYTHM MANAGEMENT SYSTEM WITH ARRHYTHMIA PREDICTION AND PREVENTION," Girouard et al., U.S. patent application Ser. No. 10/213,268 entitled, "CARDIAC RHYTHM MANAGEMENT SYSTEMS AND METHODS PREDICTING CONGESTIVE HEART FAILURE STATUS," or Brockway et al., U.S. patent application Ser. No. 10/889,353 entitled, "EXPERT SYSTEM FOR PATIENT MEDICAL INFORMATION ANALYSIS," each of which are assigned to Cardiac Pacemakers, Inc. and recite the use of conditional probabilities to predict the likelihood of occurrence of a future event. In the present context, the future event is a disease state, such as heart failure, and the circadian rhythms sensed or received serve as triggers/markers or, more generally, the conditioning events. The weights correlating each circadian rhythm representative signal to a future disease state are conditional probabilities that may alternatively be expressed as rates, as described in the above-incorporated Sweeney et al. reference.

Figure 5:
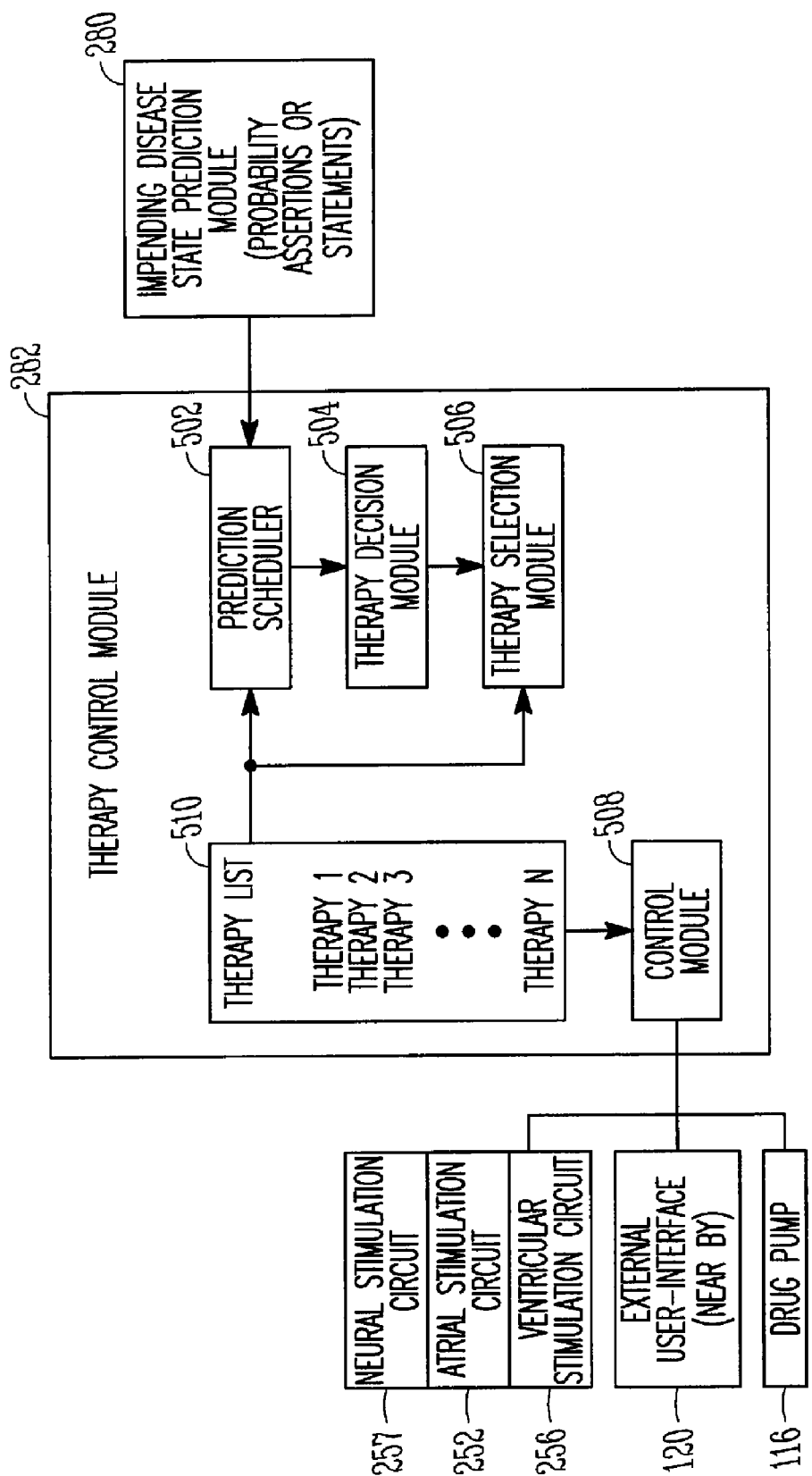
FIG. 5 is a block diagram illustrating one conceptual example of a therapy control module.

FIG. 5 is a block diagram illustrating one conceptual example of a therapy control module 282, which may be used to trigger one or more therapies to a subject 110 (FIG. 1) in response to a predicted occurrence of an impending disease state. The therapy control module 282 includes an input that receives the probability assertions or statements output from the impending disease state prediction module 280. In one example, a prediction scheduler 502 schedules the predictions of impending disease, such as heart failure. A therapy decision module 504 decides whether therapy is warranted. The therapy selection module 506 selects one or more appropriate therapies. The control module 508 adjusts the selected therapy via an output to one or more of an atrial stimulation circuit 252, a ventricular stimulation circuit 256, a neural stimulation circuit 257, a nearby external user-interface 120, or a drug pump 116, for example. The therapy control module 282 further includes a therapy list 510, which may include means to relate the therapies of the therapy list 510 to the circadian rhythms used by the impending disease state prediction module 280 in predicting the occurrence of impending heart failure, for example. The various submodules in the therapy control module 282 are illustrated as such for conceptual purposes only; however, these submodules may alternatively be incorporated in the impending disease state prediction module 280 or elsewhere. As discussed below, such as in associated with FIG. 6, a subject's 110 (FIG. 1) response to the applied therapy may be monitored via the subject's post-therapy circadian rhythms.

In one example, the therapy selection module 506 selects a heart failure preventive therapy using outputs from the therapy decision module 504. If the therapy decision module 504 determines that the degree and confidence in the impending disease state prediction warrants some therapy, then the therapy selection module 506 selects a member of the therapy list 510 to be invoked. In another example, the therapy section module 506 selects a therapy that is only secondarily related to the predicted disease state.

In another example, the therapy list 510 includes all possible disease state preventive therapies or secondarily related therapies that system 100 (FIG. 1) may deliver or communicate to the subject 110. The therapy list 510 may be programmed into the IMD 102 either in hardware, firmware, or software. In yet another example, the therapy list 510 includes immediate, short-term, intermediate-term, or long-term heart failure preventive therapies. Immediate heart failure preventive therapies include, by way of example, initiating or changing a drug therapy administered to a subject 110 via an implantable drug pump 116 or electrical stimulation administered to the subject 110 via one or more electrode bearing leads 108. Short-term heart failure preventive therapies include, by way of example, administering a continuous positive air pressure ("CPAP") dose to the subject 110 or notifying a caregiver to initiate or change the subject's drug treatment program. Intermediate-term heart failure preventive therapies include, by way of example, adjusting the subject's 110 (FIG. 1) lifestyle (e.g., decrease salt or water consumption). Finally, long-term heart failure preventive therapies include, by way of example, notifying the subject 110 or caregiver to alter the drug which takes longer to affect the subject (e.g., beta blockers, ACE inhibitors) or administering CRT to the subject.

Each member of the therapy list 510 may be associated with a required time of action, which includes one or more of a time for the therapy to become effective or a time after which the therapy is no longer effective. Accordingly, in one example, the prediction scheduler 502 considers only those members of the therapy list 510 that can be expected to be effective within a time frame commensurate with the prediction time period. In another example, only one member of the therapy list 510 is invoked at any particular time. In a further example, combinations of different therapies are provided at substantially the same time.

Figure 6:
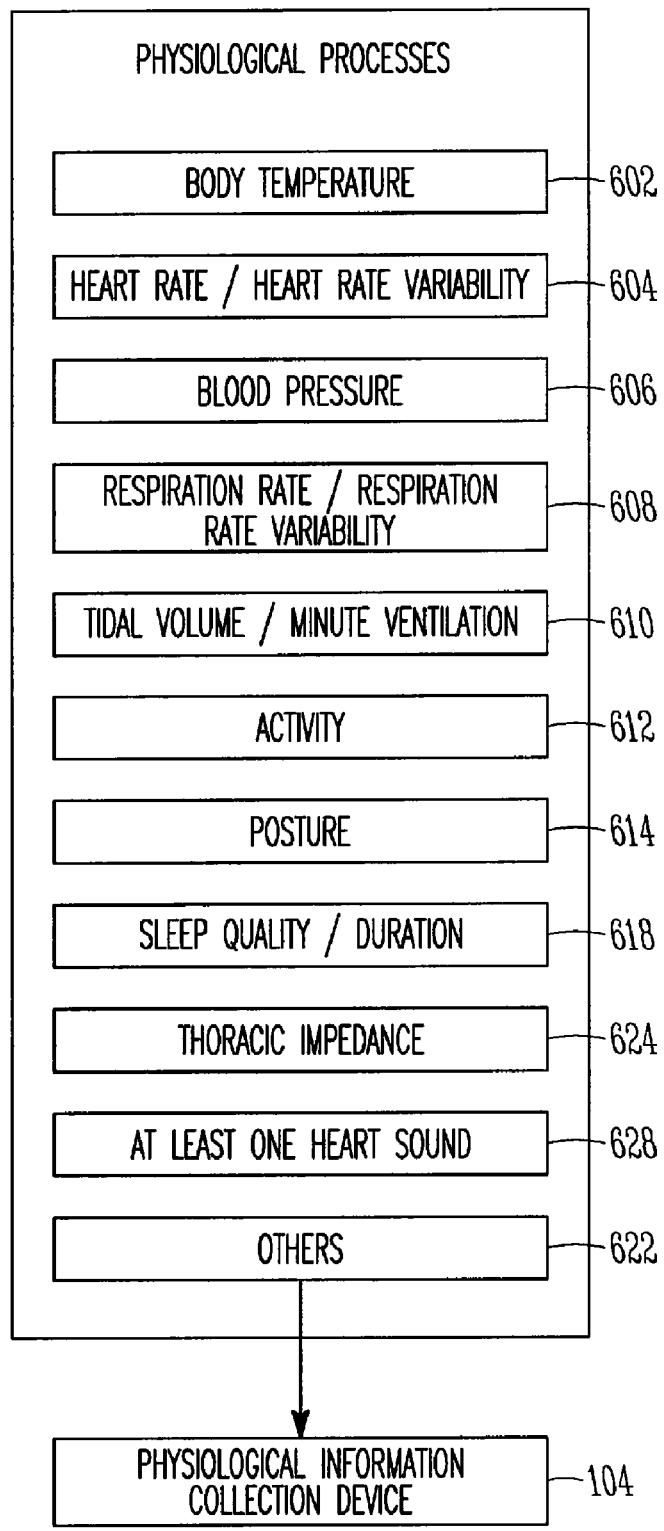
FIG. 6 is a block diagram illustrating exemplary physiological processes having circadian rhythms that may be used to predict, monitor, or treat an occurrence of impending heart failure or other disease state in a subject.

FIG. 6 is a block diagram illustrating exemplary physiological processes of a subject 110 (FIG. 1) having circadian rhythms, which when lost or changed from a baseline, may be associated with an occurrence of impending heart failure or other disease state. In varying examples, one or more of the circadian rhythms associated with the physiological processes 602-628 are used to predict, monitor, or treat an occurrence of impending heart failure in the subject 110. In certain examples, time detectors, such as a time of the circadian rhythm representative signals sensed or received, an arrhythmia incidence, or a clinical event, are used additionally or alternatively to predict, monitor, or treat the occurrence of impending heart failure. While the following discusses exemplary physiological processes 602-628 having circadian rhythms whose presence, absence, or baseline change is statistically associated with an occurrence of impending heart failure, the list is not meant to be exhaustive, and may include other processes 622 not herein discussed.

In one example, the subject's peripheral or core body temperature 602 is used as a physiological process having a certain circadian rhythm, which when lost or changed from a baseline, may be associated with impending heart failure. In healthy subjects, the human body temperature follows a definite circadian rhythm. For instance, in the late afternoon, a healthy subject's body temperature can be as much as 2° F. higher than in the morning. This circadian rhythm, however, may begin to become less pronounced or otherwise change several hours to several days before the onset of a disease state, such as heart failure. Monitoring the circadian rhythm associated with body temperature in such instances and comparing the results to one or more baseline prediction criteria derived from one or more subjects in a non-disease state, provides a tool to predict, monitor, or treat an occurrence of impending heart failure. In one example, the circadian rhythm associated with the subject's body temperature is measured by a temperature sensor 260 (FIG. 2), such as a temperature capsule embedded under the skin.

In another example, the subject's heart rate or heart rate variability ("HRV") 604 is used as a physiological process having a certain circadian rhythm, which when lost or changed from a baseline, may be associated with impending heart failure. In healthy subjects having HRV, the heart rate intervals have a circadian rhythm, with HRV generally increasing during periods of sleep. This circadian rhythm, however, may become less pronounced, more irregular, or otherwise change several hours to several days before the onset of a disease state, such as heart failure. Monitoring HRV in such instances and comparing the variability to one or more baseline prediction criteria derived from one or more subjects in a non-disease state, provides a tool to predict, monitor, or treat an occurrence of impending heart failure. In one example, the circadian rhythm associated with HRV is determined by standard deviation, variance, or other characteristic indicative of variability. In another example, the circadian rhythm associated with HRV is measured by a heart rate/heart rate variability sensor 266 (FIG. 2).

In a similar manner, the subject's heart rate may also be used in the prediction of impending heart failure. In healthy subjects, the heart rate follows a certain circadian rhythm. For instance, a healthy subject's heart rate is typically lower during the sleep hours than during the awake hours. This circadian rhythm, however, may become lost or change from a baseline several hours to several days before the onset of a disease state, such as heart failure. In many instances, heart rate 604 during sleep may actually increase before the onset of the disease state and lower frequency components of HRV 604 associated with abnormal sympathetic activation may also increase.

In another example, the subject's blood pressure 606 is used as a physiological process having a certain circadian rhythm, which when lost or changed from a baseline, may be associated with impending heart failure. In healthy subjects, blood pressure follows a circadian rhythm. For instance, the blood pressure typically rises in the morning and stays elevated until late afternoon, at which time it drops off and hits its lowest point during the night. This circadian rhythm, however, may begin to become less pronounced or otherwise change several hours to several days before the onset of a disease state, such as heart failure. Monitoring the circadian rhythm associated with blood pressure in such instances and comparing the results to one or more baseline prediction criteria derived from one or more subjects in a non-disease state, provides a tool to predict, monitor, or treat an occurrence of impending heart failure. In one example, the circadian rhythm associated with the subject's blood pressure is measured by a blood pressure sensor 258 (FIG. 2).

In another example, the subject's respiratory rate or respiratory rate variability ("RRV") 608 is used as a physiological process having a certain circadian rhythm, which when lost or changed from a baseline, may be associated with impending heart failure. In healthy subjects, the respiratory rate variability follows a circadian rhythm. This circadian rhythm, however, may become lost or change from a baseline several hours to several days before the onset of a disease state, such as heart failure. Indications of a loss or baseline change of circadian rhythm may include a low frequency component of the subject's respiratory rate decreasing (as the subject is less likely to be active), and a high frequency component increasing. Monitoring respiratory rate in such instances and comparing the variability to one or more baseline prediction criteria derived from one or more subjects in a non-disease state, provides a tool to predict, monitor, or treat an occurrence of impending heart failure. In one example, the circadian rhythm associated with RRV is measured by a respiratory rate sensor 262 (FIG. 2). In one such example, the respiratory rate sensor 262 includes an implantable breathing rate module which includes a fiducial point detector adapted to detect a fiducial point on the breathing signal that occurs a known number of one or more times during the breathing cycle and a timer measuring the time interval between respective successive fiducial points. In another such example, the respiratory rate sensor 262 includes an implantable transthoracic impedance sensor to peak-detect, level-detect, or otherwise detect impedance variations resulting from breathing, such as is described in Dalal et al., U.S. patent application Ser. No. 11/458,602 entitled, "SLEEP STATE DETECTION," which is assigned to Cardiac Pacemakers, Inc.

In another example, the subject's tidal volume or minute ventilation ("MV") 610 is used as a physiological process having a certain circadian rhythm, which when lost or changed from a baseline, may be associated with impending heart failure. In healthy subjects, tidal volume and MV follow a circadian rhythm. For instance, when plotted on a number of events vs. MV counts histogram graph, an upper portion of a MV histogram represents daytime MV, while a lower portion represents nighttime MV. This circadian rhythm, however, may begin to become less pronounced or otherwise change several hours to several days before the onset of a disease state, such as heart failure. Monitoring the circadian rhythm associated with tidal volume or minute ventilation in such instances and comparing the results to one or more baseline prediction criteria derived from one or more subjects in a non-disease state, provides a tool to predict, monitor, or treat an occurrence of impending heart failure. In one example, the circadian rhythm associated with the subject's tidal volume or minute ventilation is measured by an internal sensor 262 (FIG. 2), such as a rate detector and an impedance sensor.

In another example, the subject's activity level 612 is used as a physiological process having a certain circadian rhythm, which when lost or changed from a baseline, may be associated with impending heart failure. In healthy subjects, activity level follows a circadian rhythm. This circadian rhythm, however, may begin to become less pronounced or otherwise change several hours to several days before the onset of a disease state, such as heart failure. Indications of a loss or baseline change of circadian rhythm may include a decrease in the subject's activity level. Monitoring the circadian rhythm associated with activity level in such instances and comparing the results to one or more baseline prediction criteria derived from one or more subjects in a non-disease state, provides a tool to predict, monitor, or treat an occurrence of impending heart failure. In one example, the circadian rhythm associated with the subject's activity level is measured by an activity level sensor 270 (FIG. 2). In another example, the circadian rhythm associated with the subject's activity level is measured using, at least in part, an indication of activity level input into a nearby external user interface 120 (FIG. 2) by the subject.

In another example, the subject's posture 614 is used as a physiological process having a certain circadian rhythm, which when lost or changed from a baseline, may be associated with impending heart failure. In healthy subjects, posture follows a circadian rhythm. This circadian rhythm, however, may begin to become less pronounced, more irregular, or otherwise change several hours to several days before the onset of a disease state, such as heart failure. Indications of a loss or baseline change of circadian rhythm may include the subject's increasingly supine posture orientation. Monitoring the circadian rhythm associated with posture in such instances and comparing the results to one or more baseline prediction criteria derived from one or more subjects in a non-disease state, provides a tool to predict, monitor, or treat an occurrence of impending heart failure. In one example, the circadian rhythm associated with the subject's posture is measured by a posture sensor 268 (FIG. 2), such as a two-axis accelerometer having Model No. ADXL202E, manufactured by Analog Device, Inc. of Norwood, Mass., U.S.A. In another example, the subject's posture is measured using techniques described in Hatlestad et al., U.S. patent application Ser. No. 10/267,982, entitled "DETECTION OF CONGESTION FROM MONITORING PATIENT RESPONSE TO RECUMBENT POSITION," which is also assigned to Cardiac Pacemakers, Inc.

In another example, the pattern of the subject's wake/sleep cycle 618 is used as a physiological process having a certain circadian rhythm, which when lost or changed from a baseline, may be associated with impending heart failure. In healthy subjects, sleep patterns follow an organized circadian rhythm. For instance, one is most likely to sleep soundly when his/her temperature is lowest, in the early morning hours, and most likely to awaken when his/her temperature starts to rise around 6:00-8:00 am. This circadian rhythm, however, may begin to become less organized several hours to several days before the onset of a disease state, such as heart failure. Monitoring the circadian rhythm associated with sleep patterns 618 in such instances and comparing the results to one or more baseline prediction criteria derived from one or more subjects in a non-disease state, provides a tool to predict, monitor, or treat an occurrence of impending heart failure.

The circadian rhythm associated with the subject's wake/sleep cycle 618 may be measured by an internal sleep detector 272 (FIG. 2), which in some examples determines both the amount of quality of the subject's sleep. One example of a sleep detector is described in Carlson et al., U.S. patent application Ser. No. 09/802,316 entitled, "CARDIAC RHYTHM MANAGEMENT SYSTEM USING TIME-DOMAIN HEART RATE VARIABILITY INDICIA," which is assigned to Cardiac Pacemakers, Inc. Another example of a sleep detector is described in Dalal et al., U.S. patent application Ser. No. 11/458,602 entitled, "SLEEP STATE DETECTION," which is assigned to Cardiac Pacemakers, Inc. Yet another example of a sleep detector is described in Ni et al., U.S. patent application Ser. No. 10/309,771 entitled, "SLEEP DETECTION USING AN ADJUSTABLE THRESHOLD," which is assigned to Cardiac Pacemakers, Inc. Alternatively, the subject 110 or caregiver may enter an indication of his/her sleep quality or duration into an external user interface 120 or 122 (FIG. 2).

In another example, the subject's thoracic impedance 624 is used as a physiological process having a certain circadian rhythm, which when lost or changed from a baseline, may be associated with impending heart failure. In healthy subjects, thoracic impedance 624 follows a circadian rhythm in which impedance is lower during the night and early morning hours and higher during the mid-to-date afternoon. This circadian rhythm, however, may begin to shift, become less pronounced, or otherwise change several hours to several days before the onset of a disease state, such as heart failure. Monitoring the circadian rhythm associated with thoracic impedance 624 and comparing the results to one or more baseline prediction criteria derived from one or more subjects in a non-disease state, provides a tool to predict, monitor, or treat an occurrence of impending heart failure. In one example, the circadian rhythm associated with the subject's thoracic impedance 624 is measured by injecting an electrical stimulus current of known or attainable value (e.g., via the ventricular 256 or atrial 252 stimulation circuits) to one or more implanted electrodes and measuring (e.g., via the ventricular 254 or atrial 250 sense circuits) the resulting voltage using one or more other implanted electrodes. Using information about the current and the resulting voltage, the IMD 102 may calculate an impedance by taking a ratio of resulting voltage to injected current.

In yet another example, the subject's heart sounds 628 (for example, heart sounds referred to in the art as $S_1$, $S_2$, and particularly the heart sound referred to in the art as $S_3$) are used as a physiological process having a certain circadian rhythm, which when lost or changed from a baseline, may be associated with impending heart failure. In healthy subjects, heart sounds 628 follow a circadian rhythm. This circadian rhythm, however, may begin to become less pronounced, change frequency, or otherwise change several hours to several days before the onset of a disease state, such as heart failure. In one example, the circadian rhythm associated with the subject's heart sounds 628 is measured by an implantable accelerometer, microphone or other implantable sensor, such as by using the systems and methods described by Lincoln et al., U.S. Pat. No. 6,665,564 entitled, "CARDIAC RHYTHM MANAGEMENT SYSTEM SELECTING A-V DELAY BASED ON INTERVAL BETWEEN ATRIAL DEPOLARIZATION AND MITRAL VALVE CLOSURE," or the systems and methods described in Lincoln et al., U.S. patent application Ser. No. 10/099,865 entitled, "CARDIAC RHYTHM MANAGEMENT SYSTEM AND METHOD USING TIME BETWEEN MITRAL VALVE CLOSURE AND AORTIC EJECTION," each of which is assigned to Cardiac Pacemakers, Inc. In another example, the heart sounds 628 are measured by a caregiver while the subject is lying on his/her side, and a numerical value indicative of a heart sound frequency of amplitude is input into an external user interface 120, 122 (FIG. 2), by the caregiver.

Alternatively or additionally, a time of the circadian rhythm representative signals sensed or received, an arrhythmia incidence, or a clinical event may be used to predict, monitor, or treat an occurrence of impending disease. As one example, the time of a subject's clinical event is entered into an external user-interface 120, 122 and used to predict, monitor, or treat the occurrence of impending disease. Admissions to the emergency room for pulmonary edema not associated with acute myocardial infarction is highest between 8:00 am-Noon and 8:00 pm-12:00 am and lowest between Noon-8:00 pm. Thus, clinical admission in combination with a reduced body temperature 602 in the late afternoon, for instance, may indicate the onset of a disease state, such as heart failure.

As another example, the time of a subject's arrhythmia or abnormal breathing incidence (e.g., apnea, hypopnoea, or periodic breathing) is used to predict, monitor, or treat the occurrence of impending disease. A cardiac arrhythmia incidence is any disorder of the heart rate or rhythm. The presence of one or more cardiac arrhythmias may correlate to an occurrence of impending heart failure. In one example, as discussed above, the IMD 102 (FIG. 2) may utilize an atrial 252 (FIG. 2) and ventricular 254 (FIG. 2) sensing circuit to sense cardiac signals for determining whether a rhythm is normal or pathologic. In another example, the subject or caregiver enters a detected presence of one or more cardiac arrhythmia, found using an echocardiogram or other imaging instrument, into an external user interface 120 or 122 (FIG. 2).

Figure 7A:
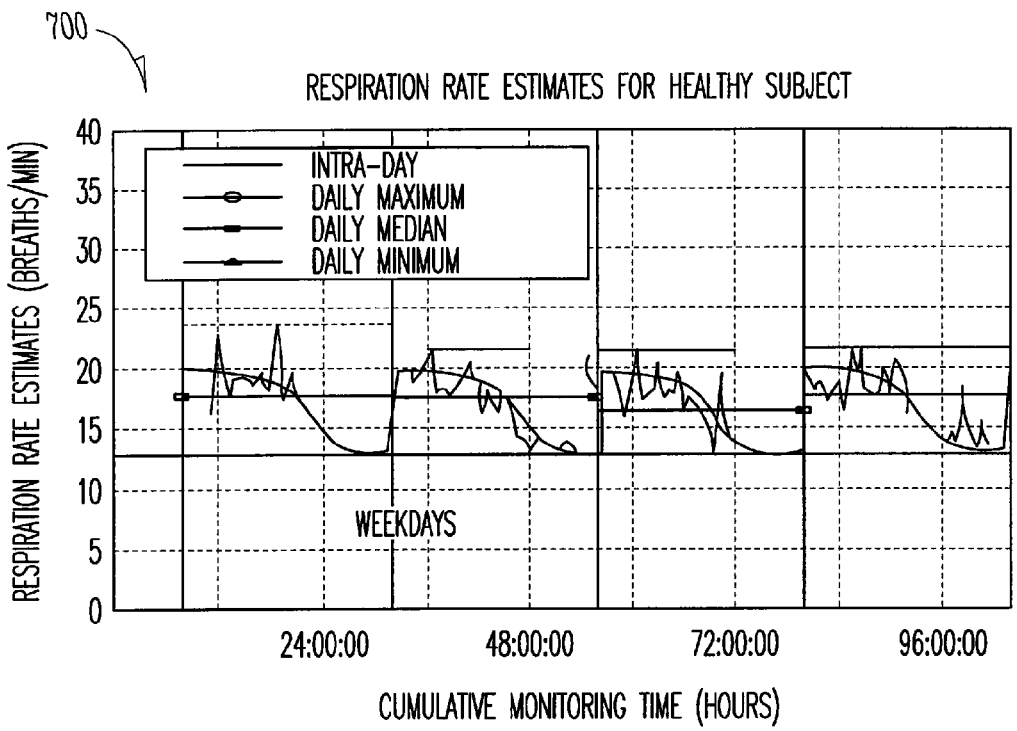
FIGS. 7A-7C are graphical illustrations that may be used by a subject or caregiver to predict, monitor, or treat an occurrence of impending heart failure or other disease state in the subject.
Figure 7A:
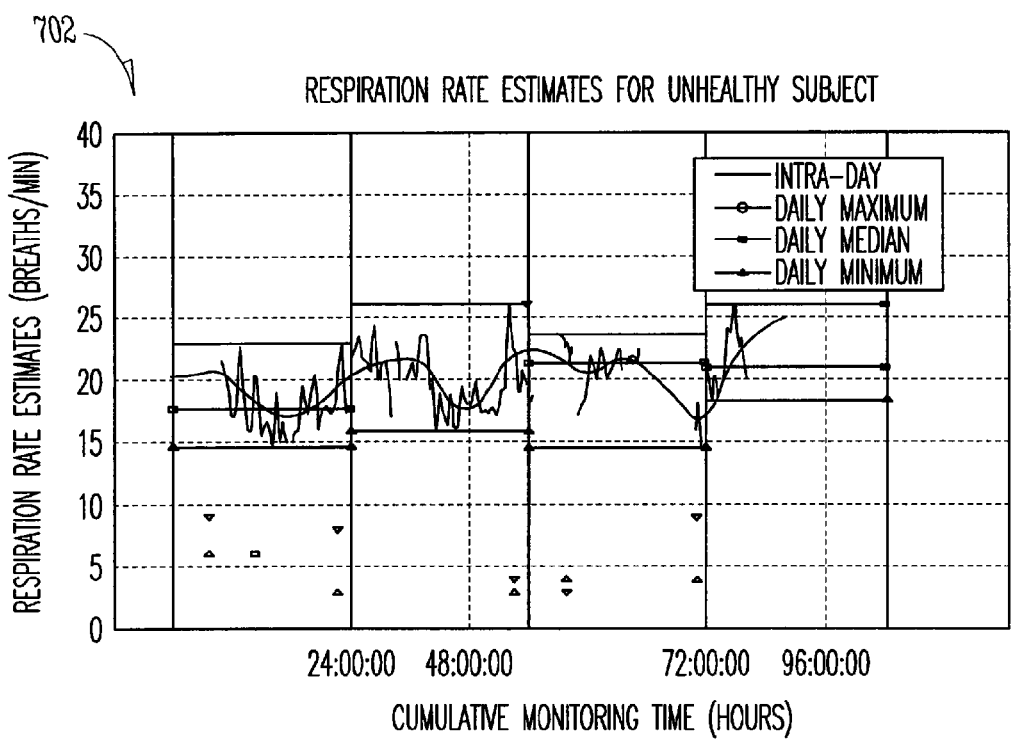
Figure 7B:
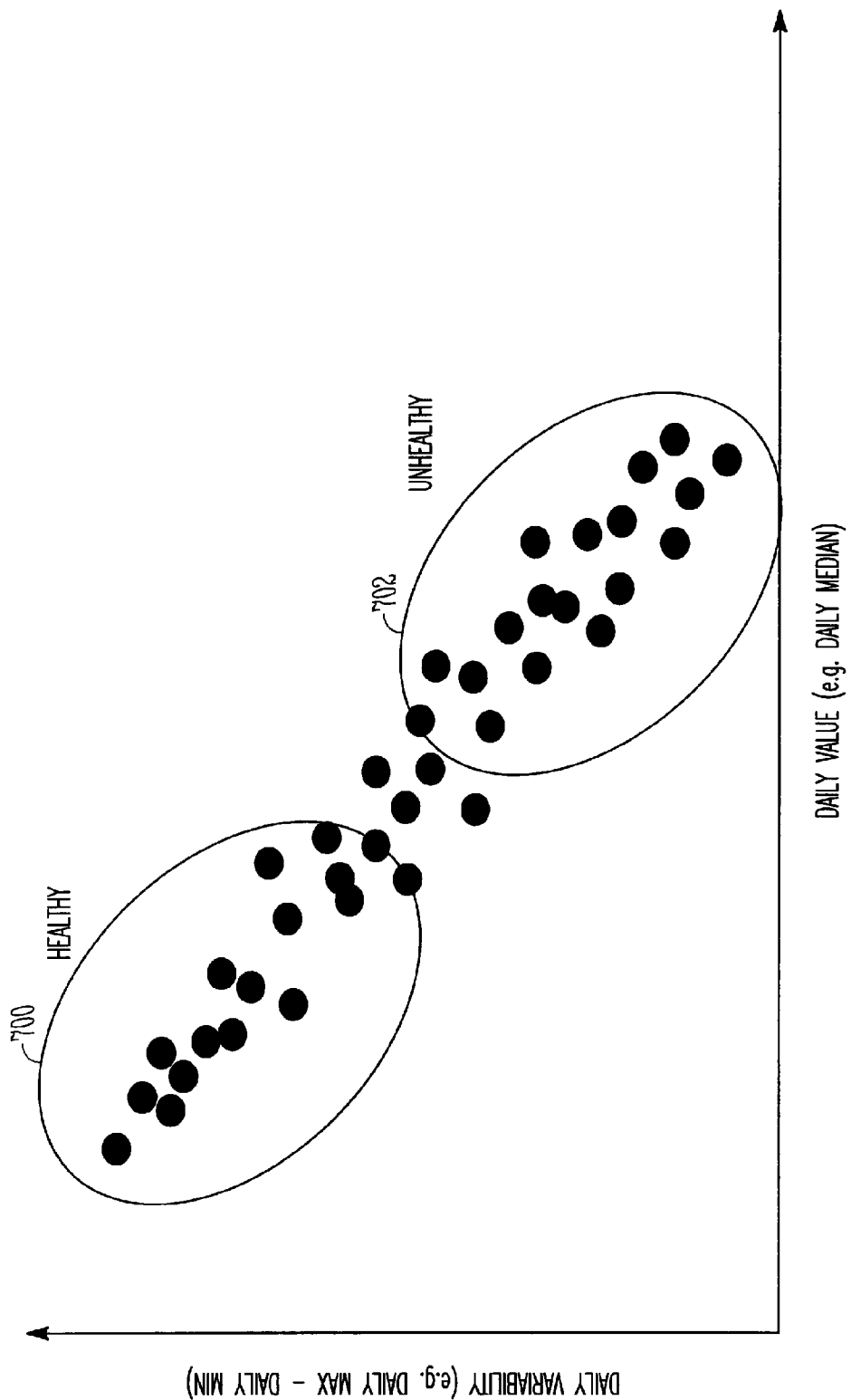
Figure 7C:
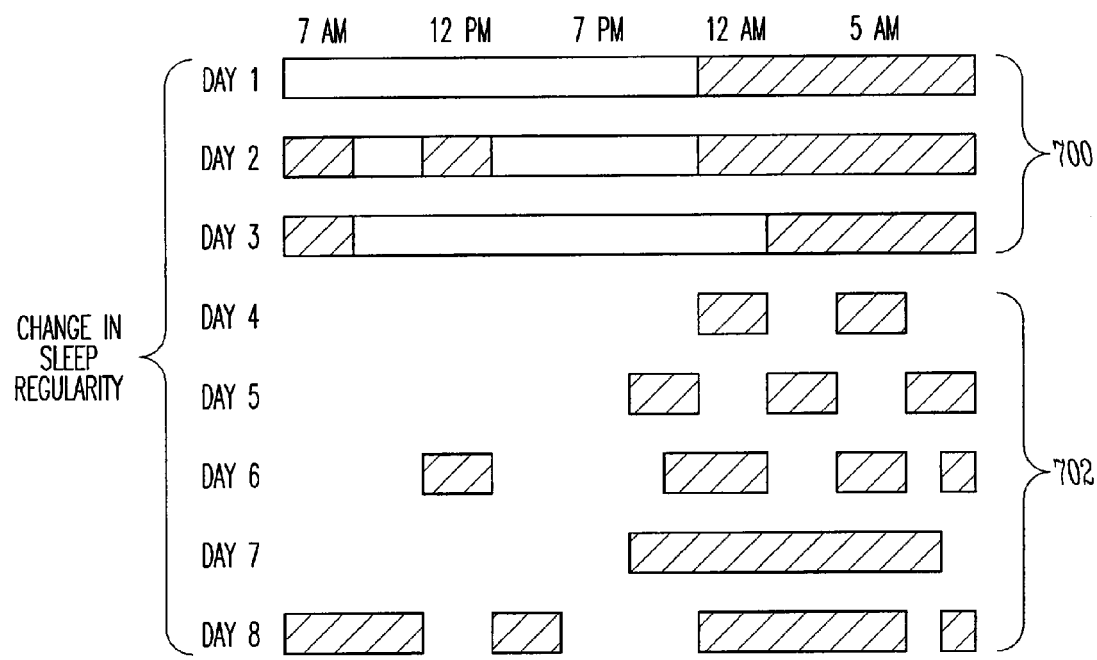

FIGS. 7A-7C illustrate exemplary graphs that may be generated by system 100 and which illustrate circadian rhythm comparisons that may be made between circadian rhythms associated with at least one physiological process sensed or received and one or more baseline circadian rhythm prediction criteria. These illustrations, when displayed on an external user interface 120, 122 display screen (FIG. 1), for example, may be used by a subject 110 (FIG. 1) or caregiver to predict, monitor, or treat an occurrence of impending heart failure or other disease state.

FIG. 7A illustrates circadian rhythms associated with respiration rate 608 (FIG. 6) plotted on a respiration rate (breaths/minute) vs. time (hours) graph. As shown, the respiration circadian rhythm of a healthy subject 700 includes a pronounced, regular pattern; whereas, the respiration circadian rhythm of an unhealthy subject 702 includes a less pronounced and irregular pattern. More specifically, the unhealthy subject has a higher maximum respiratory rate, a higher mean/median respiratory rate, and less variability in minimum/mean/median respiratory rate in comparison to the healthy subject. Since the respiration circadian rhythm of the unhealthy subject 702 is lost or changed relative to the healthy subject's baseline circadian rhythm 700, a prediction of impending disease, such as heart failure, may have been in order for the unhealthy subject as soon as such loss or change can be made with a reasonable degree of certainty.

FIG. 7B illustrates an alternative way to graphically illustrate circadian rhythms associated with respiration rate 608 (FIG. 6) of a healthy and unhealthy subject. In FIG. 7B, conceptualized (i.e., not real) data of the daily variability of the respiratory rate is plotted against the daily median of the respiratory rate. In this conceptualization, the healthy subject 700 maintains a lower median respiratory rate and higher variability in the mean respiratory rate than the unhealthy subject 702. Among other things, such characteristics of the healthy subject may indicate an easier time breathing and a greater activity level than the unhealthy subject.

FIG. 7C illustrates a circadian rhythm associated with a subject's wake/sleep cycle 618 (FIG. 6). Initially, on days 1-3, the subject follows a substantially regular sleep schedule, including sleeping from about 12:00-5:00 am each day. Such regular sleep schedule is indicative of a healthy subject 700. In contrast, on days 4-8, the subject follows a very irregular sleep schedule. For instance, on day 4, the subject sleeps from about 12:00-1:00 am and 4:30-5:30 am. Then, on day 5, the subject sleeps from about 9:00 pm-12:00 am, 1:00-4:30 am, and from 5:30-6:00 am. Such irregular sleep schedule is indicative of a unhealthy subject 702.

Subjects with severe heart failure often suffer from inability to sleep either due to pulmonary congestion or inability to tolerate a supine posture. In addition, evidence from sleep studies indicate that as a person nears death, the time in which the subject sleeps becomes much more fragmented. By visually seeing the sleep regularity (or irregularity, as it may be), caregivers (or the subject themselves) may be able to determine if the subject's health state is changing due to a possible worsening in disease state. Since the sleep circadian rhythm of the unhealthy subject 702 is lost or changed relative to the healthy subject's baseline circadian rhythm 700, a prediction of impending disease, such as heart failure, may have been in order for the unhealthy subject as soon as such loss (marked by irregularity) could be made with a reasonable degree of certainty.

Figure 8:
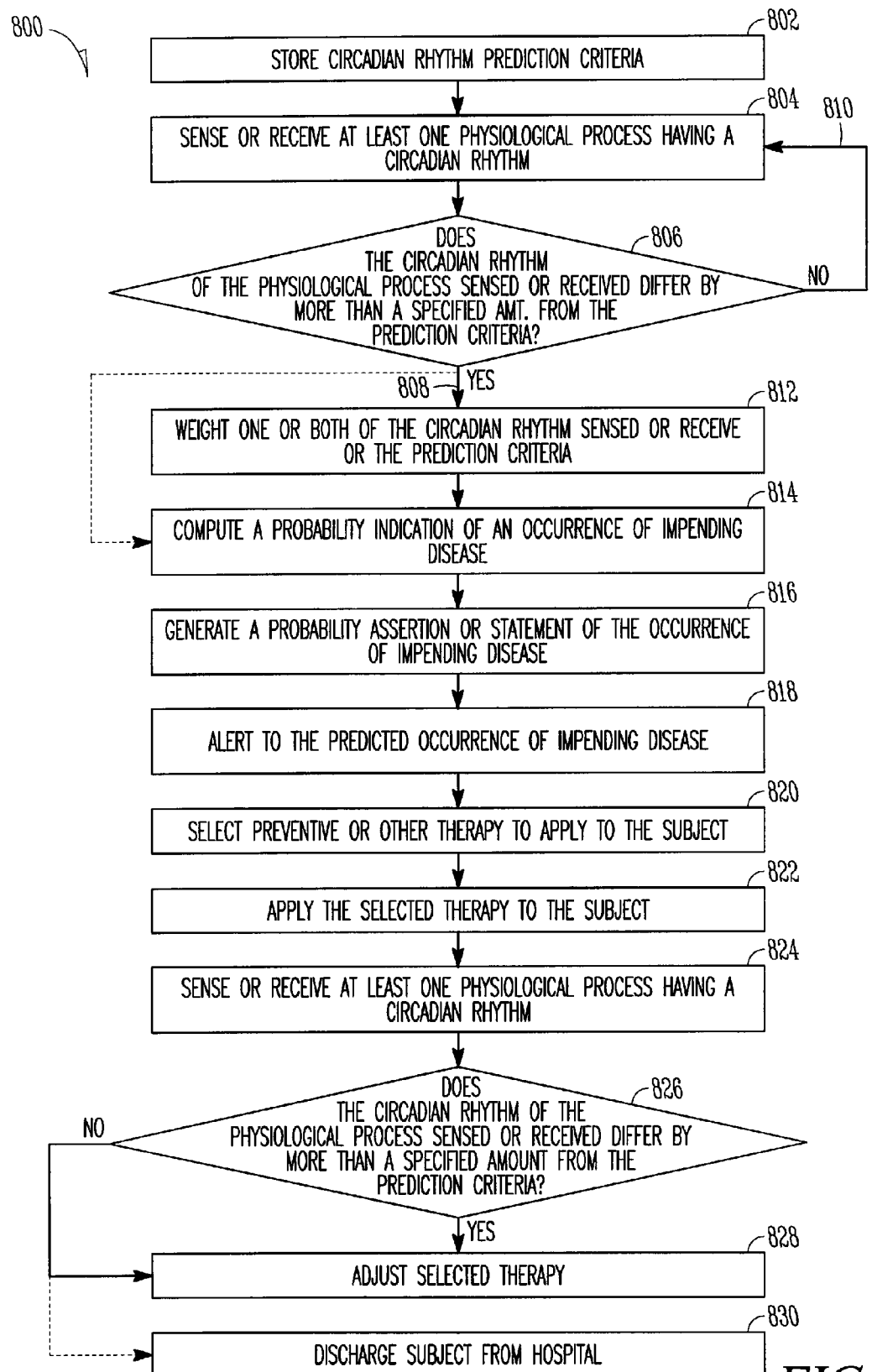
FIG. 8 illustrates a method of predicting, monitoring, or treating an occurrence of impending heart failure or other disease state in a subject.

FIG. 8 illustrates one example of a method 800 of predicting, monitoring, or treating an occurrence of impending disease, such as heart failure, in a subject. At 802, one or more baseline circadian rhythm prediction criteria are stored. This may be accomplished in a number of ways. In one example, the one or more baseline circadian rhythm prediction criteria are loaded into an IMD before, during, or after the IMD is implanted in the subject. The one or more baseline circadian rhythm prediction criteria may be established in a number of ways. In one example, the one or more baseline circadian rhythm prediction criteria are derived using one or more past physiological process observation of the subject when in a non-disease health state. In another example, the one or more baseline circadian rhythm prediction criteria are derived using one or more past physiological process observation of a population in a non-disease health state.

At 804, at least one physiological process having a circadian rhythm whose presence, absence, or baseline change is statistically associated with a disease state, is sensed or received. This may be accomplished in a number of ways. In one example, the at least one physiological process having the circadian rhythm is sensed or received via a physiological information collection device. The circadian rhythm representative signals sensed or received may be associated with various physiological processes, such as body temperature (core or peripheral), heart rate, heart rate variability, respiration rate, respiration rate variability, minute ventilation, activity, blood pressure, posture, tidal volume, sleep quality or duration, thoracic impedance, or heart sounds.

At 806, the circadian rhythm associated with the at least one physiological process sensed or received is compared with the one or more baseline circadian rhythm prediction criteria. This may be accomplished in a number of ways. In one example, a probability comparator of an impending disease state prediction module compares one or more sensed or received circadian rhythm representative signal $(S_1, S_2, \ldots, S_N)$ values to corresponding baseline circadian rhythm prediction criteria $(C_1, C_2, \ldots, C_N)$ values. When the values of the circadian rhythm representative signals sensed or received differ by more than a specified amount from the baseline circadian rhythm prediction criteria, thereby indicating a loss or baseline change of circadian rhythm, a positive probability indication of the occurrence of impending heart failure results at 808. When the values of the circadian rhythm representative signals sensed or received are substantially similar to the baseline circadian rhythm prediction criteria, therefore indicating no substantial loss or baseline change of circadian rhythm, a negative probability indication of the occurrence of impending heart failure results at 810 and the process returns to 804.

Optionally, at 812, each circadian rhythm representative signal $(S_1, S_2, \ldots, S_N)$ value differing from the corresponding baseline circadian rhythm prediction criteria $(C_1, C_2, \ldots, C_N)$ value by more than the specified amount is weighted. This may be accomplished in a number of ways. In one example, for each circadian rhythm representative signal $(S_1, S_2, \ldots, S_N)$ value differing from the corresponding baseline circadian rhythm prediction criteria $(C_1, C_2, \ldots, C_N)$ value by more than the specified amount, a weighting module of the impending disease state prediction module stores weighting factors $(Weight_1, Weight_2, \ldots, Weight_N)$. In another example, each weighting factor $(Weight_1, Weight_2, \ldots, Weight_N)$ provides a degree to which each circadian rhythm representative signal differing from the corresponding baseline circadian rhythm prediction criteria by more than the specified amount enters into a probability indication computed at 814. In yet another example, each weight is computed using not only information about which physiological process the circadian rhythm relates to, but also using information about which other physiological processes having circadian rhythms are also being used to predict the occurrence of impending heart failure.

At 816, a probability assertion or statement of impending heart failure is made. This may be accomplished in a number of ways. In one example, a prediction processing module of the impending disease state prediction module generates, using the probability indication output, a probability assertion or statement that a heart failure will occur (e.g., within a specified time period after the prediction). In another example, at least one of the sensing or receiving, comparing, or predicting is performed, at least in part, implantably.

At 818, an alert of the predicted occurrence of impending heart failure decompensation is provided to the subject or a caregiver. The alert may be communicated in a number of ways. In one example, an audible tone is sounded. In another example, the subject is linked up to a remote monitoring system (e.g., via a communication repeater) thereby allowing the alert to be electronically communicated to the caregiver for review. In yet another example, muscle tissue in the locality of the IMD within the subject is stimulated. In a further example, the alert includes transmitting information about the predicted occurrence of impending heart failure and information used to make the prediction to an external user interface.

In this way, the information used to make the prediction may be presented to the subject or caregiver on the interface's LCD or other display.

At 820, one or more appropriate therapies are selected (e.g., drug therapy or neurostimulation). In one example, one or more heart failure preventive therapy is selected. In another example, one or more therapy secondarily related to heart failure is selected. The therapy selection may be accomplished in a number of ways. In one example, a therapy selection module selects the one or more appropriate preventive or other therapies. At 822, a therapy is initiated using the predicted occurrence of impending heart failure (e.g., within a specified prediction time period). This may be accomplished in a number of ways. In one example, an control module activates the selected therapy via an output to a an atrial stimulation circuit, a ventricular stimulation circuit, a neural stimulation circuit, or a drug pump.

By monitoring post-therapy circadian rhythms, the efficacy and necessary amount of therapy may be determined. To this end, at least one physiological process having a circadian rhythm, whose presence, absence, or baseline change is statistically associated with a disease state, is sensed or received at 824. This may be accomplished in a number of ways, such as those discussed in regard to the method at 804. At 826, the circadian rhythm associated with the at least one physiological process sensed or received is compared with the one or more baseline circadian rhythm prediction criteria, such as at 806. When the values of the circadian rhythm representative signals sensed or received differ by more than a specified amount from the baseline circadian rhythm prediction criteria, an increase in the amount of selected therapy may be warranted at 828. When the values of the circadian rhythm representative signals sensed or received are substantially similar to the baseline circadian rhythm prediction criteria, a titration of the selected therapy may be warranted at 828; additionally, if applicable, a discharge of the subject from the hospital may be reasonable at 830.

CONCLUSION

Heart failure is a common clinical entity, particularly among the elderly, but is often not treated (if at all) until the disease is detected late in the disease process via associated physical symptoms, such as abnormal thoracic fluid build-up behind the heart. Advantageously, the present systems and methods allow for the prediction, monitoring, or treatment of impending heart failure or other disease states by monitoring one or more circadian rhythms associated with a subject's physiological process. Practically every physiological process in the human body exhibits circadian rhythmicity, and thus, the monitoring of circadian rhythm provides an adequate means for predicting, monitoring, or treating an impending disease state, such as heart failure or heart failure decompensation, among others.

The time savings provided by prediction (as opposed to detection alone), may reduce or eliminate expensive hospitalization and aid in avoiding a decompensation crisis or properly managing a heart failure subject, for example, in a state of relative well-being. Further, the present systems and methods provide an alert to the subject or the subject's caregiver regarding a positive prediction of impending heart failure or other disease state. Further yet, the present systems and methods may adjust (or initiate) a therapy (e.g., drug therapy or neurostimulation) to prevent or minimize impending disease state using the prediction and monitor the efficacy of such therapy (including monitoring the subject's recovery).

While the present systems and methods may be used to monitor process rhythms on a variety of cycle periods, such as circadian, circaseptan, circatrigintan, circannual, holidays, weekdays, weekends, or menstrual, collectively "chronobiological rhythms", a majority of the foregoing description is cast in terms of circadian rhythm monitoring for exemplary purposes. Such description is not intended, however, to limit the scope of the present subject matter in any way. Furthermore, a loss or baseline change of chronobiological (e.g., circadian) rhythm may signify an occurrence of an impending disease state other than just heart failure. For instance, a breakdown in chronobiological rhythm may occur during general sickness (e.g., a flu or cold), neurological, mental or pulmonary disease, a viral or bacterial infection, other cardiovascular diseases (e.g., diabetes) or even cancer. As such, this patent document is intended to be commensurate in scope to cover these additional embodiments.

It is to be understood that the above description is intended to be illustrative, and not restrictive. For example, the above-described embodiments (or aspects thereof) may be used in combination with each other. Many other embodiments will be apparent to those of skill in the art upon reviewing the above description. The scope of the present systems and methods should therefore, be determined with reference to the appended claims, along with the full scope of legal equivalents to which such claims are entitled. In the appended claims, the term "including" is used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. A system comprising:
   a prediction criteria module, adapted to store information about one or more chronobiological rhythm prediction criteria;
   a physiological information collection device, adapted to sense or receive information about at least one physiological process having a chronobiological rhythm whose presence, absence, or change is statistically associated with a disease state;
   an impending disease state prediction module, coupled to the prediction criteria module to receive the one or more chronobiological rhythm prediction criteria and coupled to the physiological information collection device to receive the chronobiological rhythm of the at least one physiological process, the impending disease state prediction module being adapted to predict an occurrence of impending disease using the one or more chronobiological rhythm prediction criteria and the chronobiological rhythm of the at least one physiological process; and at least one of the prediction criteria module, the physiological information collection device, or the impending disease state prediction module including an implantable portion; wherein the predicted occurrence of impending disease is computed using one or more stored weighting factors, each weighting factor corresponding to a chronobiological rhythm of a different one of the at least one physiological processes.

2. The system of claim 1, wherein the impending disease state prediction module is adapted to predict that an occurrence of impending disease will occur during a specified prediction time period after the prediction.

3. The system of claim 1, wherein the information about the at least one physiological process is sensed or received, at least in part, using an implantable device or sensor.

4. The system of claim 1, wherein the at least one physiological process includes one or more of body temperature, heart rate, heart rate variability, respiration rate, respiration rate variability, minute ventilation, tidal volume, activity, blood pressure, posture, sleep pattern, thoracic impedance, or at least one heart sound.

5. The system of claim 4, further comprising a timing circuit coupled to the physiological information collection device to provide an associated collection time to the chronobiological rhythm of the at least one physiological process; and wherein the associated collection time is used by the impending disease state prediction module to predict the occurrence of impending disease.

6. The system of claim 1, further comprising an arrhythmia detector adapted to sense or receive information about an arrhythmia incidence; and wherein a time of the arrhythmia incidence is used by the impending disease state prediction module to predict the occurrence of impending disease.

7. The system of claim 1, wherein the chronobiological rhythm prediction criteria are derived using one or more past physiological process observation from a subject in a non-disease state.

8. The system of claim 1, further comprising a therapy control module adapted to adjust or initiate a therapy using the predicted occurrence of impending disease.

9. The system of claim 8, further comprising an implantable drug pump, coupled to the therapy control module to receive one or more drug delivery instruction.

10. The system of claim 8, further comprising a neural stimulation circuit, coupled to the therapy control module to receive one or more neurostimulation delivery instruction.

11. The system of claim 8, further comprising at least one of a ventricular or atrial stimulation circuit, coupled to the therapy control module to receive one or more cardiac stimulation delivery instruction.

* * * * *